(12) United States Patent
Bartunek et al.

(10) Patent No.: US 7,794,758 B2
(45) Date of Patent: Sep. 14, 2010

(54) COMPOUNDS AND METHODS FOR PROMOTING CELLULAR HEALTH AND TREATMENT OF CANCER

(75) Inventors: Arthur W. Bartunek, New York, NY (US); Robert L. Bard, New York, NY (US)

(73) Assignee: PMC Formulas, Inc. NY (US)

( * ) Notice: Subject to any disclaimer, the term of this patent is extended or adjusted under 35 U.S.C. 154(b) by 0 days.

(21) Appl. No.: 12/099,109

(22) Filed: Apr. 7, 2008

(65) Prior Publication Data

US 2008/0248129 A1    Oct. 9, 2008

Related U.S. Application Data

(60) Provisional application No. 60/910,457, filed on Apr. 5, 2007.

(51) Int. Cl.
*A61K 36/87* (2006.01)
*A61K 36/00* (2006.01)

(52) U.S. Cl. ............................. 424/725; 424/766
(58) Field of Classification Search .................. None
See application file for complete search history.

(56) References Cited

U.S. PATENT DOCUMENTS

| | | | | |
|---|---|---|---|---|
| 5,910,308 A * | 6/1999 | D'Jang | ..................... | 424/729 |
| 5,932,561 A * | 8/1999 | Meyers et al. | ............... | 514/55 |
| 6,399,116 B1 * | 6/2002 | Xiu | ............................ | 424/773 |
| 6,436,406 B1 * | 8/2002 | Yegorova | ............... | 424/195.16 |
| 6,509,372 B2 * | 1/2003 | Bok et al. | ................... | 514/456 |
| 6,541,046 B2 * | 4/2003 | Wei et al. | ..................... | 424/756 |
| 2002/0016314 A1 * | 2/2002 | Schersl | ..................... | 514/169 |
| 2005/0142231 A1 * | 6/2005 | Gong et al. | ................. | 424/762 |
| 2005/0214383 A1 * | 9/2005 | Bubnis et al. | .............. | 424/641 |
| 2006/0003947 A1 * | 1/2006 | Udell | ........................... | 514/26 |
| 2008/0267938 A1 * | 10/2008 | Olalde Rangel | ........... | 424/94.1 |

FOREIGN PATENT DOCUMENTS

CN    1418556 A    *    5/2003
JP    11-269082    *    10/1999

OTHER PUBLICATIONS

Registry entry for betaine—1984.*
http://www.uniprot.org/taxonomy/4081—accessed Jan. 2009.*
http://www.hort.purdue.edu/newcrop/nexus/eutrema_wasabi_nex.html—accessed Jan. 2009.*
http://plants.usda.gov/java/profile?symbol=ROOF—accessed Jan. 2009.*
http://plants.usda.gov/java/profile?symbol=ELAEI—accessed Jan. 2009.*
http://plants.usda.gov/java/profile?symbol=VITIS—accessed Jan. 2009.*

* cited by examiner

*Primary Examiner*—Patricia Leith
(74) *Attorney, Agent, or Firm*—Dylan O. Adams; Graybeal Jackson LLP

(57) ABSTRACT

Systems and methods are provided herein that provide for promoting cellular health and treatment of cancer, and allied diseases such as diabetes and glaucoma.

1 Claim, 26 Drawing Sheets
(24 of 26 Drawing Sheet(s) Filed in Color)

|  | Effective Range | | Percent of Total | |
| --- | --- | --- | --- | --- |
|  | Low Mg. | High Mg. | Low | High |
| Gynostemma pentaphy lum 12:1 | 30/360 | 240/2880 | 3.41% | 4.03% |
| Astragalus Root 10:1 | 22.5/225 | 180/1800 | 2.56% | 3.03% |
| Ligustrum fruit 10:1 | 18.75/187.5 | 180/1800 | 2.13% | 3.03% |
| Schisandra fruit 10:1 | 22.5/225 | 180/1800 | 2.56% | 3.03% |
| Rhodiloa Rosea 20:1 (50/50) | 15/300 | 120/2400 | 1.70% | 2.02% |
| Rhodiloa Crenulata 15:1 (50/50) | 15/225 | 120/1800 | 1.70% | 2.02% |
| Pomegranate 70% ellagic acid | 70 | 420 | 7.06% | 7.95% |
| Polygonum cuspidatum 15% resveratrol | 15 | 90 | 1.51% | 1.70% |
| Quercetin | 50 | 300 | 5.04% | 5.68% |
| Phytosterol Complex | 360 | 2400 | 40.34% | 40.88% |
| IP6 Powder | 74.375 | 510 | 8.57% | 8.45% |
| TMG | 30 | 240 | 4.03% | 3.41% |
| OPC Grapeseed Extract | 12 | 96 | 1.61% | 1.36% |
| Lycopene Extract 15% | 5 | 30 | 0.50% | .57% |
| I-OptiZinc Powder | 5 | 30 | 0.50% | .57% |
| Copper (as gluconate) | .5 | 3 | 0.50% | .06% |
| Lecithin Powder | 50 | 300 | 5.04% | 5.68% |

*Table 1*

|  | Effective Range | | Percent of Total | |
| --- | --- | --- | --- | --- |
|  | Low Mg. | High Mg. | Low | High |
| Gynostemma pentaphy lum 12:1 | 30/360 | 240/2880 | 3.41% | 4.03% |
| Astragalus Root 10:1 | 22.5/225 | 180/1800 | 2.56% | 3.03% |
| Ligustrum fruit 10:1 | 18.75/187.5 | 180/1800 | 2.13% | 3.03% |
| Schisandra fruit 10:1 | 22.5/225 | 180/1800 | 2.56% | 3.03% |
| Rhodiloa Rosea 20:1 (50/50) | 15/300 | 120/2400 | 1.70% | 2.02% |
| Rhodiloa Crenulata 15:1 (50/50) | 15/225 | 120/1800 | 1.70% | 2.02% |
| Pomegranate 70% ellagic acid | 70 | 420 | 7.06% | 7.95% |
| Polygonum cuspidatum 15% resveratrol | 15 | 90 | 1.51% | 1.70% |
| Quercetin | 50 | 300 | 5.04% | 5.68% |
| Wasabia japonica 15:1 | 20 | 420 | 7.06% | 7.95% |
| Palm Oil Tocotrienols | 15 | 90 | 1.51% | 1.70% |
| Phytosterol Complex | 360 | 2400 | 40.34% | 40.88% |
| Rosemary 10% Carnosic Acid | 15 | 90 | 1.51% | 1.70% |
| IP6 Powder | 74.375 | 510 | 8.57% | 8.45% |
| TMG | 30 | 240 | 4.03% | 3.41% |
| OPC Grapeseed Extract | 12 | 96 | 1.61% | 1.36% |
| Lycopene Extract 15% | 5 | 30 | 0.50% | .57% |
| I-OptiZinc Powder | 5 | 30 | 0.50% | .57% |
| Copper (as gluconate) | .5 | 3 | 0.50% | .06% |
| Lecithin Powder | 50 | 300 | 5.04% | 5.68% |

*Table 2*

COMPOUNDS AND METHODS FOR PROMOTING CELLULAR HEALTH AND TREATMENT OF CANCER

RELATED REFERENCES

This application claims priority to U.S. Provisional Application 60/910,457 filed Apr. 5, 2007. The foregoing application is hereby incorporated by reference in its entirety as if fully set forth herein.

FIELD

This invention relates generally to therapeutic compounds, and more specifically, to compounds and methods for promoting cellular health and treatment of cancer, and allied diseases such as diabetes and glaucoma.

BACKGROUND

The prostate gland (or prostate) is a walnut-sized, mucous-producing organ in males that lies just below the urinary bladder. The prostate typically grows starting at puberty until about the age of 30, when equilibrium is established between cell growth and apoptosis. Hormonal changes later in life, when coupled with diets that do not provide adequate nutrition for the prostate cells and hormonal system, may retrigger growth, leading to benign prostatic hypertrophy, or abnormal enlargement of the prostate. The only known function of the prostate is to produce a secretion that nourishes and protects sperm during reproduction. The urethra passes through the prostate gland. Hypertrophy or hyperplasia of the prostate may affect the function of the urethra, usually by occlusion of the urethra.

In men, the prostate gland is the source of several common disorders including prostatitis and benign prostatic hypertrophy ("BPH"), wherein the prostate gland becomes inflamed or enlarged. Prostatitis is defined as an inflammation or infection of the prostate gland. While prostatitis may be acute, associated with systemic findings of fever, chills and rigors, most cases of prostatitis are chronic and tend to be incurable with relatively frequent recurrences despite optimal standard medical therapy. Chronic prostatitis (inflammation or infection of the prostate) is common to all adult men. It is associated with virtually all cases of prostate cancer and is present in every prostate biopsy regardless of other findings.

In the early phase of prostatic enlargement, the bladder muscle has to force urine through the narrowed urethra by contracting more forcefully. Over a period of time, this forcing causes the bladder muscle to become stronger, thicker, and overly sensitive. In some cases, as prostate enlargement progresses and the urethra is squeezed more tightly, the bladder cannot overcome the problems created by the narrowed urethra. If this occurs, the bladder cannot empty completely. This situation creates a need to urinate more frequently. In a small percentage of men, incomplete emptying of the bladder may lead to repeated urinary tract infections, sudden inability to urinate, or gradual bladder and/or kidney damage. An enlarged prostate may even result in total blockage of the urethra, which a very serious condition.

Prostatitis encompasses any form of inflammation of prostate tissue. Only a relatively small percent is caused by bacterial infection, and increasing evidence suggests a link to sex steroid hormones. However, any chronic inflammation of the prostate is now suspected to be a risk factor for prostate cancer. Elevated levels of the inflammatory cytokine IL-8 promotes stromal and epithelail cell proliferation and is up-regulated in both BPH and aiPCa. IL-8 is also implicated in angiogenesis. This suggests a potentially causative link between prostatitis and PCa, and, while there is no causative association between BPH and PCa, a possible underlying mechanism common to both BPH and aiPCa. Vitamin D has been shown to be able to suppress the production of IL-8. These studies, therefore, support the proposition that treatments to reduce BPH and prostatitis, and the inclusion of dietary agents that potentate the effects of vitamin D3 on IL-8, will also reduce the incidence and progression of prostate cancer.

Prostate cancer is the third most common cause of death from cancer in men of all ages and is the most common cause of death from cancer in men over 75 years old. Prostate cancer is rarely found in men younger than 40. Men at higher risk include black men older than 60, farmers, tire workers, painters, and men exposed to cadmium. The lowest incidence occurs in Greece and several other areas of the Mediterranean, with rates among Japanese men about halfway between Greek men and men consuming a typical western diet. While diets in low incidence areas are high in vegetables and some fruits, vegetarian diets alone do not reduce incidence or mortality, as shown in a study of mortality rates for British vegetarians. Nutritional content of locally grown produce and fruits, herbs, and other components of the diets are more significant than gross meal composition. The cause of prostate cancer is unknown, although studies have shown a relationship to overall diet and lifestyle (i.e. Greek vs. Western Diets), obesity, metabolic syndrome, and hormone imbalances.

Prostate cancer is a serious and often life-threatening condition. It is characterized by rapidly-proliferating cell growth and continues to be the subject of worldwide research efforts directed toward the identification of therapeutic agents are effective in the treatment thereof. Effective therapeutic agents prolong the survivability of the patient, inhibit the rapidly-proliferating cell growth associated with the disease, or effect a regression of the disease. Research in this area is primarily focused on identifying agents are therapeutically effective in humans and other mammals. Therapeutic effectiveness may be measured most quickly by assessing blood flow diminution in tumors that have demonstrable blood flow pretreatment. This test is most accurately performed by employing Doppler ultrasound flows (Cornud F, Am J Radiol 74:1161, 2000).

Common therapies for prostate cancer include prostatectomy, radiation, cryotherapy, and/or chemotherapy. More recently, the University Hospital of Belgium conducted a study showing antioxidants retarded the growth of many malignant and premalignant tumors. For patients with metastatic diseases, androgen deprivation via chemical or surgical means remains the last treatment modality. With passing time, however, cancer often becomes refractory to hormone ablation, leaving patients with metastatic disease no other conventional treatment options. These patients often seek unconventional "alternative" and/or "complementary" treatments, most commonly herbal therapies (phytotherapies). Such use is dramatically rising in recent years both in the U.S. and in Europe. The number of patients undergoing treatment with alternative medicine in the U.S. increased from 34% in 1990 to 42% in 1997. This number is still rising and there are now more visits to alternative health practitioners than total visits to all primary care physicians combined.

Many of these therapies seek to correct deficiencies or imbalances that may be present in a subject. For example, research suggests that low Coenzyme Q10 ("Q10") levels may be linked to various types of cancers. One study compared 27 women with normal Pap smears with 75 women with cervical cancer and its precursor—cervical intraepithelial neoplasia. It was found that women with cervical cancer and neoplasia had lower concentrations of cervical/vaginal cell Q10 and vitamin E (alpha-tocopherol) compared to women with normal Pap smears. (Mikhail MS, et al. Coenzyme Q10 and a-tocopherol concentrations in cervical intraepithelial neoplasia and cervix cancer. Obstet Gynecol 2001;97).

In another study, 200 French women with malignant and non-malignant breast tumors were found to have reduced amounts of Q10 in their blood despite normal concentrations of vitamin E. (Jolliet P, et al. Plasma coenzyme Q10 concentrations in breast cancer: prognosis and therapeutic consequences. Fund Clin Pharmacol 1997;11).

In a still further study 21 Turkish women who underwent radical mastectomies for breast cancer found lower levels of Q10 within the breast tumor compared to the normal surrounding tissue. Four of the women had no detectable amounts of Q10 in the tumor or nearby tissue. (Portakal O, et al. Coenzyme Q10 concentrations and antioxidant status in tissues of breast cancer patients. Clin Biochem 2000;33:279-84).

Unfortunately, simply providing cancer patients with only supplements, such as Q10, is not sufficient in many cases because a supplement alone may lack cellular-bioavailability and/or function. Accordingly, formulations may need to address issues such as absorption, bioavailability, and activity in addition to supplementation of a deficiency.

BRIEF DESCRIPTION OF THE DRAWINGS AND TABLES

The patent or application file contains at least one drawing executed in color. Copies of this patent or patent application publication with color drawing(s) will be provided by the office upon request and payment of the necessary fee.

The present invention will be described by way of exemplary embodiments but not limitations, illustrated in the accompanying drawings in which like references denote similar elements, and in which.

Figure 1:
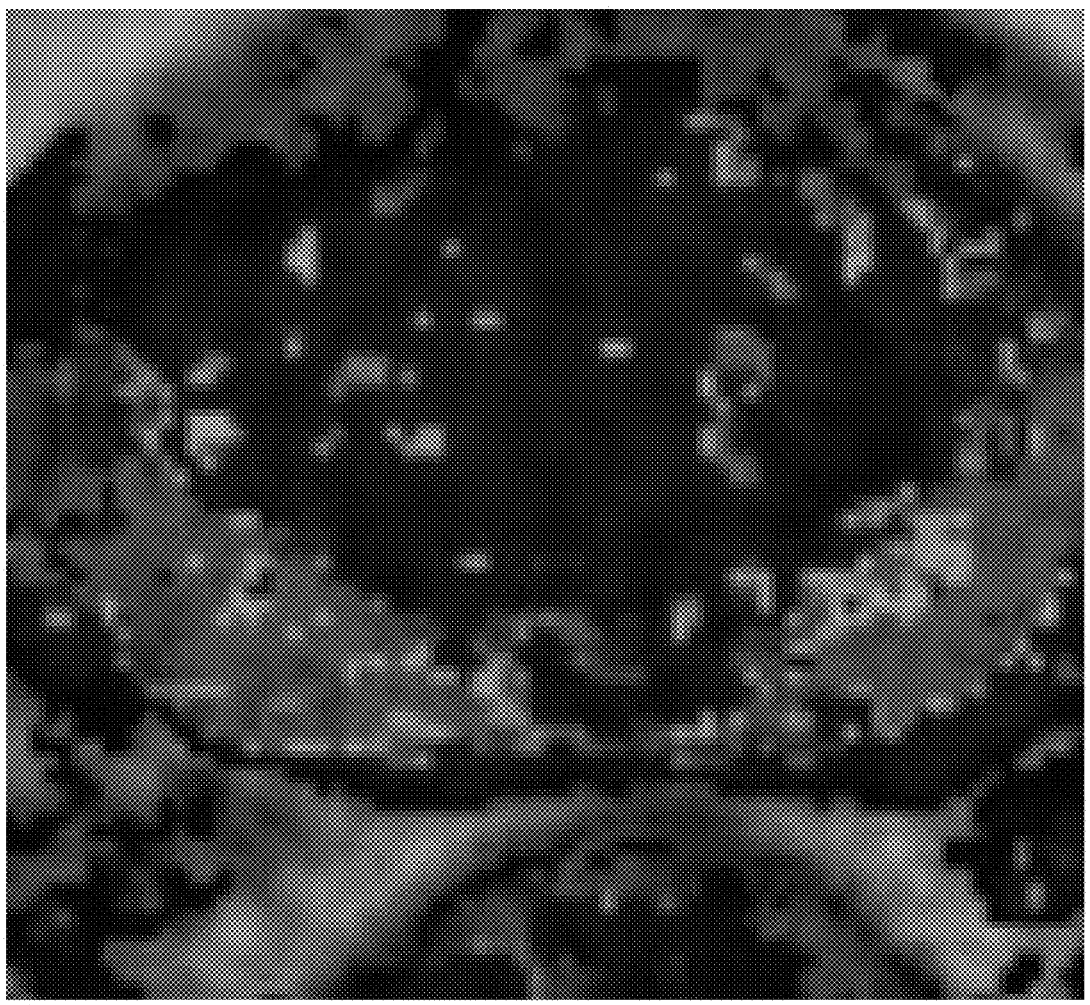
FIG. 1 depicts an image of the prostate of an exemplary subject before treatment with a therapeutic composition, in accordance with an embodiment.

TABLE 1 depicts an exemplary therapeutic composition that may be used to treat human male subjects for diseases or disorders or to promote cellular health, in accordance with one embodiment of the invention.

TABLE 2 depicts an exemplary composition that may be used to treat a female human subject for diseases including breast cancer, or any other cancer, and/or promote cellular health in accordance with one embodiment of the invention.

DESCRIPTION

This invention relates generally to therapeutic compounds, and more specifically, to compounds and methods for promoting cellular health and treatment of cancer.

Various aspects of the illustrative embodiments will be described using terms commonly employed by those skilled in the art to convey the substance of their work to others skilled in the art. However, it will be apparent to those skilled in the art that the embodiments described herein may be practiced with only some of the described aspects. For purposes of explanation, specific numbers, materials and configurations are set forth in order to provide a thorough understanding of the illustrative embodiments. However, it will be apparent to one skilled in the art that the embodiments described herein may be practiced without the specific details. In other instances, well-known features are omitted or simplified in order to not obscure the illustrative embodiments.

Further, various operations and/or communications will be described as multiple discrete operations and/or communications, in turn, in a manner that is most helpful in understanding the embodiments described herein; however, the order of description should not be construed as to imply that these operations and/or communications are necessarily order dependent. In particular, these operations and/or communications need not be performed in the order of presentation.

The phrase "in one embodiment" is used repeatedly. The phrase generally does not refer to the same embodiment; however, it may. The terms "comprising," "having" and "including" are synonymous, unless the context dictates otherwise.

The term "therapeutically effective amount" and related terms as used herein refer to that amount of extract or compound which will contribute to the therapeutic ability of the composition, which may include, but is not limited to treatments for benign prostate hyperplasia (BHP), prostatitis, prostate cancer, cancer of any organ or system of a subject and allied diseases such as diabetes and glaucoma. Additionally, this may apply to treatments for cellular health of one or more organ or system of a subject.

The term "treating," or any similar term, including but not limited to "treat", "treatments" or "treated," as used herein relating to cancer, for example, refers to partial or total inhibition of the growth, spreading, or metastasis of prostate cancer, cancer of various organs or systems of a subject, partial or total destruction of the cancer cells, and the like The term "treating" may include the reduction or elimination of prostate cancer, cancer of various organs or systems of a subject, the reduction in the incidence of the disease, and the like.

The term "treating" also may include the reduction, stabilization, regression, elimination of benign prostate hyperplasia or prostatitis, and the like. The term "treating" may include the reduction, stabilization, regression or elimination of allied diseases such as diabetes, glaucoma, and the like. The term "treating" may also include the promotion of cellular health in one or more organ or system of a subject, and the like.

The term "preventing" or any similar term, including but not limited to "prevent", "prevents" or "prevented," as used herein may refer to preventing the onset of prostate cancer, cancer of various organs or systems of a subject, benign prostate hyperplasia or prostatitis, preventing the onset of a pre-clinically evident stage of said diseases or disorders in a subject at risk for said disorders, and the like. Also intended to be encompassed by this definition is the prevention of initiation for malignant cells, the arrest or reversal of the progression of pre-malignant cells to malignant cells, and the like. "Preventing" may also include the prevention of growth or spreading of prostate cancer or other cancer. This includes prophylactic treatment of those at risk of developing a prostate cancer or other cancer. "Preventing" also may include the prevention of growth or spreading of other allied diseases, such as diabetes, glaucoma, and the like.

The term "subject" as used herein may refer to any human or mammal subject that has prostate cancer, cancer of various organs or systems, benign prostate hyperplasia, prostatitis, and the like. For methods of prevention, the subject may be any human or animal subject that is at risk for developing prostate cancer, cancer of any organ or system, benign prostate hyperplasia or prostatitis. The subject may be at risk due to exposure to carcinogenic agents, being genetically predisposed to have any of these diseases or disorder, and the like.

Compounds and Methods for Promoting Cellular Health and Treatment of Cancer

This following description and figures relate generally to therapeutic compounds, and more specifically, to compounds and methods for promoting cellular health, promoting optimal organ function, the treatment of cancer, treatment of allied diseases such as diabetes and glaucoma, and the like. In one embodiment, there may be a synergistic composition for preventing and treating benign prostatic hyperplasia, prostatitis, prostate cancer and for promoting cellular health, which includes an effective amount of phytosterols, quercetin, resveratrol and extract from *Gynostemma pentaphyllum*; *Astragalus* root; and *Punica granatum*. In another embodiment, a composition can further include an effective amount of inositol hexaphosphate; trimethylglycine; zinc; copper; salidroside; and extract from *Schisandra* fruit. Additionally, in a further embodiment, a composition can further include an effective amount of lycopene and extract from *Ligustrum* fruit. Furthermore, in a still further embodiment, a composition can comprise an effective amount of extract from *Wasabia japonica*; trocotrienols; carnosic acid; oligomeric proanthocyanidins; lecithin; and extract from *Rhodiola crenulata*.

In various embodiments, compositions can be such that the lycopene may be a concentration of, or extraction from the plant *Solanum lycopersicum*, trocotrienols may be from extract from a plant of the genus *Elaeis*, oligomeric proanthocyanidins may be from an extract from the plant of the genus *Vitis*, and the carnosic acid may be from an extract from the plant *Rosmarinus officinalis*, which may be concentrated such that the extract comprises about 10% carnosic acid. Furthermore, in some embodiments, a composition can be such that phytosterols comprise at least 50% or 38% by weight of beta-sitosterol; additionally, resveratrol may be from an extract from *Polygonum cuspidatum*.

In other embodiments, combinations of compounds and certain plants or herbs properly extracted and blended in appropriate proportions may be used in treating cancer, prostate disorders, and in the promotion of cellular health, including but not limited to benign prostatic hyperplasia, prostatitis, prostate cancer, breast cancer, melanoma, allied diseases such as diabetes and glaucoma, and the like.

Accordingly, various embodiments relate to methods for treating said diseases or disorders in a subject, comprising the step of administering an effective amount of a composition to the subject to treat or prevent a given disorder or disease, wherein the composition comprises therapeutically effective amounts of compounds or extracts as described herein. In one embodiment, a composition is administered orally. In another embodiment, the orally administered composition is in the form of one or more capsules, one or more soft-gel, one or more tablet, or one or more pill.

While many cancer treatments tend to address discrete aspects of cell cycle control, promoting cellular health and proper nutrition targets a subject's own cell cycle regulatory systems that control both normal cell reproduction and the immune system's elimination of improperly reproduced cells, which may ultimately lead to the development of cancer. Compromised cell membrane integrity along with increased membrane rigidity and alteration of the isoprenoid pathway are three key aspects of cancer development that may be addressed through nutrition.

Cellular membrane integrity and increased cellular membrane rigidity may be addressed by treatment with phytosterols and extracts from *Gynostemma pentaphyllum*, which protects cellular membranes from oxidative injury by reversing decreased cellular membrane fluidity. Additionally, in the presence of phytosterols, the mean fluidity of a cellular membrane may be regulated.

In another embodiment, cellular membrane integrity and increased cellular membrane rigidity may be addressed by treatment with phytosterols and a gensenoside or an extract from a plant of the class *Panax*, which may include *Panax quinquefolium*, Ginseng, *Panax ginseng* (Chinese *ginseng*), *Panax notoginseng* (Sanchi), *Panax japonicus* (Rhizoma Panacis Majoris), *Panax quinquefolium* L. (American *ginseng*), and *P. ginseng* (Korean *ginseng*)

With regard to alteration of the isoprenoid pathway, the alteration of the balance of calcium and magnesium may be desirable in various embodiments, and may be addressed by *Rhodiola rosea*, the extract of which may comprise salidroside, which may normalize the cell environment by suppressing the excessive entry of Ca2+ and the release of calcium stores. Therefore, phytosterols (including, beta-sitosterol, beta-sitostanol and campesterol), *Gynostemma pentaphyllum*, and salidroside or an extract of *Rhodiola rosea*, or plants of the genus *Rhodiola*, which comprises salidroside, or an extract of *Rhodiola rosea* may be used to increase cell membrane integrity in a subject and allow normal function as a semi-permiable membrane and thereby help to both maintain and restore regulation of membrane fluidity as well as the balance of calcium and magnesium in a subject. A paper presented by Dr. Neil Fleshner, MD, MDP, FRCSC entitled ACTIVE SURVEILANCE:OPPORTUNITY FOR TERTIARY PREVENTION IN PROSTATE CANCER was presented at the 2007 American Society of Clinical Oncology's PROSTATE CANCER SYMPOSIUM indicating a variety of agents have been demonstrated to reduce the growth rates of prostate cancer and combinations perform better than single ingredients. Thus, additionally, one or more additional herb, food, or compound may be selected to act synergistically with each other or one or more phytosterol and salidroside.

In various embodiments, maintaining calcium ($Ca^{2+}$) balance and cell membrane permeability may be desirable because it may promote more efficient and effective utilization of coenzyme Q10 ("Q10"), cycling of Q10 between the ubiquinone and ubiquinol states, and the like. One or more of treating cellular membrane integrity, treating cellular membrane elasticity, treating cellular membrane permeability, and treating a calcium imbalance may restore, promote, or increase Q10 cellular-bioavailability and/or function. In various embodiments, restoring, promoting or increasing Q10 cellular-bioavailability and/or function may be desirable because it may lead to normal morphology and membrane functionality of the cell including enzyme activity and permeability, reduced proliferation, normal cell reproduction and increased apoptosis.

For example, in one embodiment, the treatment of a cellular membrane to restore integrity, and restoration of membrane elasticity and permeability with phytosterols and *gynostemma pentaphyllum*, and the treatment with *Rhodiola rosea* to redress the $Ca^{2+}$ imbalance, may synergistically restore the function of coenzyme Q10 in intra-cellular fluids, inter-cellular fluids, in a cell's mitochondrial membrane, and the like, for metabolic regulation and/or for energy conservation. In another embodiment, at least one of normal cellular reproduction, differentiation, and programmed cell death can be restored, promoted or increased, by treatment with Q10 and one or more of, a phytosterol, *gynostemma, Rhodiola*, and the like. In one embodiment, a composition comprising beta-sitosterol and Q10 can increase or promote normal cellular reproduction, differentiation, and apoptosis.

In one embodiment, treatment with Q10 can use one or more forms of Q10, including ubiquinone, ubiquinol, and the like. In another embodiment, a subject can be treated with a dose of Q10 about between 100 to 1,000 milligrams per day (mg/day); however, larger doses of 1500 mg/day, 2000 mg/day, 2500 mg/day, 3000 mg/day, 3500 mg/day, or greater may be given in other embodiments. In a further embodiment, a dosage of Q10 can be varied depending on the bioavailability of the given Q10 form, or the like. For example, in another embodiment, about between 400-800 mg/day, or 600-800 mg/day of Q-absorb (Jarrow Formulas, Inc., Los Angeles, Calif.) may be provided.

(a) Selection of Compounds

Significant geographic variations and marked differences among various ethnic/racial groups with respect to the age-adjusted incidence and mortality rates for clinical prostate cancer have been observed in epidemiological studies; both environmental and genetic factors and their interplays are hypothesized to contribute to the observed variable incidence. In particular, the possible involvement of diet capable of exerting, promoting or protecting influences on the progression and establishment of clinically important prostate cancer have been proposed. An alternative explanation for the observed varied incidence of clinical prostate cancer may be that culture specificity and diversity, exemplified by food and other lifestyle preferences, maintain potentially metastatic prostate cancer in a latent state.

For example, subjects who live in areas of the world that consume both phytosterol and antioxidant rich diets have a lower incidence of cancer at all sites of the body compared to subjects in other areas of the world. Because a unique, broad spectrum of antioxidants—all of which serve additional unique functions in the body—come primarily from herbs, spices, and local foods, compositions comprising compounds that treat prostate cancer, other cancers, other prostate disorders, allied diseases such as diabetes and glaucoma, and that further promote cellular health may be selected from herbs and foods that are consumed by subjects in areas of the world with low incidence of cancer. For example, in one embodiment, compounds, herbs and foods may be selected to comprise a therapeutic composition, wherein the compounds, herbs and foods may be selected that are native to or pervasive in certain countries, areas, or cultures, including but not limited to Mediterranean areas, China, Japan, and the like. In another embodiment, amounts of compounds or extracts from foods, herbs or plants may be selected to approximately model the diets of subjects in one or more area of the world, including but not limited to the Mediterranean, China and Japan.

The multi-factorial, multi-stage nature of carcinogenesis underscores the heterogeneous and complex nature of cancer. The heterogeneity and complexity of cancer presents immense obstacles and challenges to scientists and clinicians, with respect to better understanding and clinical management of cancer. Increasingly, it is recognized that the single agent approaches, which have been traditionally and broadly applied to the treatment of malignant diseases, may be inadequate for treatment. Accordingly, concerted efforts have been mounted to better strategize combination and/or sequential therapies for treating a variety of tumors.

Herbal therapies may be considered a form of combination therapy. They differ from the single agent approach in that aggregate bioactive, inactive, and counter-active agents are present. The collective effect of these herbs and plants along with other compounds typically results in reduced toxicity, and appearance of new and novel activities. The combination of activities present in herbal therapies may be important determinants in cancer prevention/treatment since they may circumvent overlapping molecular pathways that may result in successful cancer treatment.

For example, traditional Chinese medical practices approach the treatment of diseases using a "holistic/integrative" philosophy embodying several distinct features. Contrary to the "pharmaceutical" approaches of isolating, characterizing and applying the most potent of the active principles in a mixture, the "integrative" strategy emphasizes application of the total spectrum of bioactive ingredients present in a herbal mixture and evaluates success based on the "well being/curing" of the patients as a whole. Second, Chinese herbal formulations often comprise mixtures of herbs and thus rely on "group" administration of bioactive agents to affect cellular proliferation, restore apoptosis, and regulate prostate specific gene expression, while exerting minimal, if any, sub clinical toxicity, in target cells. Based on these principals, food components and herbs may be selected for their ability to work synergistically, allowing lower effective levels of ingredients to be used to greater effect. In addition, ingredients may be selected to supply essential nutrition that may be lacking in today's western diets and provide a range of efficacy, from dietary support and prevention, to treatment, and post-treatment maintenance. Therefore, in one embodiment, two or more herbs, foods or compounds may be selected to create a synergistic effect in a subject, when the subject is treated with the two or more herbs, foods or compounds.

(b) Phytosterols

Phytosterols are a group of steroid alcohol phytochemical compounds, including but not limited to beta-sitosterol, beta-sitostanol, campesterol, cholesterol, brassicasterol, ergosterol, and the like. In one embodiment, a subject may be treated using a composition that comprises beta-sitosterol, a mixture consisting of beta-sitosterol and campesterol, a mixture of phytosterols comprising at least 50% or 38% by weight beta-sitosterol, various mixtures of various phytosterols, and the like. In one embodiment, a subject may be treated using a composition that comprises from about 40.88% to about 40.34% by weight of one or more species of phytosterol. In another embodiment a subject may be treated using a composition that comprises from about 50.88% to about 30.34% by weight of one or more species of phytosterol. In yet another embodiment a subject may be treated using a composition that comprises from about 60.88% to about 20.34% by weight of one or more species of phytosterol.

In a still further embodiment, in various compositions described above or herein, where the composition comprises beta-sitosterol, the amount of beta-sitosterol may be interchanged with beta-sitostanol, or both beta-sitostanol and beta sitosterol. Additionally, in another embodiment, the amount of beta-sitosterol may be interchanged one or more species of various phytosterols.

With regard to beta-sitosterol, it is a compound that may be found as an integral part of a cellular membrane, and may be incorporated into cellular structure when adequate amounts of beta-sitosterol are available to a cell. It may act as an antioxidant and may protect cells from lipid peroxidation. Additionally, beta-sitosterol and campesterol may act chemically as an antioxidant and as a free radical scavenger, while physically stabilizing cell membranes. Beta-sitosterol may modulate the antioxidant enzyme response by restoring the GSH/total glutathione ratio, enhancing superoxide dismutase ("SOD"), and glutathione peroxidase ("GPx") activities and impairing catalase activity; however, Cu-ZN SOD expression and activity are not affected by beta-sitosterol, while MnSOD activity may be enhanced. Accordingly, beta-sitosterol acts as a scavenger of reactive oxygen species ("ROS") such as oxygen ions, free radicals organic peroxides and inorganic peroxides, while also activating other antioxidant responses.

On the other hand, beta-sitosterol may stimulate the sphingomyelin cycle in prostate cancer cells through increased ROS activity; although, this increase in ROS activity may be decreased by antioxidants. Therefore, in one embodiment, beta-sitosterol may be administered in a composition comprising complementary antioxidants to prevent an increase in ROS activity.

In addition, with either cholesterol or beta-sitosterol administration in vitro, at low concentrations, (lower than free iron) lipid peroxidation may be decreased. At higher concentrations, both cholesterol and beta-sitosterol may cause lipid peroxidation. However, such action from beta-sitosterol may not occur when high levels are consumed in a diet from fruits and vegetables, which carry with them a rich variety of naturally occurring antioxidants. Since circulating beta-sitosterol levels increase with increased oral administration, and are not significantly regulated by the body, it may be favorable to administer beta-sitosterol along with antioxidants in some embodiments. Accordingly, in one embodiment, a subject may be treated with a composition comprising beta-sitosterol, or one or more phytosterol, along with one or more class or species of antioxidant.

In one embodiment, a subject may be treated with a composition that comprises one or more phytosterol and resveratrol. In a further embodiment, a subject may be treated with a composition that comprises one or more phytosterol and an extract of the plant *Polygonum cuspidatum*, which comprises resveratrol. In a still further embodiment, a subject may be treated with a composition that comprises an extract of the plant *Polygonum cuspidatum*, which comprises about 15%, or about 2% resveratrol and a composition of phytosterols comprising at least 50% or 38% beta-sitosterol. In yet another embodiment, a subject may be treated with a composition that comprises an extract of the plant *Polygonum cuspidatum*, which comprises about 5% to about 25% resveratrol and a composition of phytosterols comprising about 30% to about 70% beta-sitosterol.

A composition comprising beta-sitosterol and resveratrol may inhibit tumor growth via different, complimentary and synergistic actions. Beta-sitosterol induces cell cycle arrest in the G2/M phase and induces apoptosis, while resveratrol arrests prostate cancer cell growth in S-phase, inducing apoptosis. Additionally, while beta-sitosterol increases ROS production in prostate cancer cell lines, resveratrol's antioxidant activity decreases ROS activity, yielding an intermediate level of ROS activity at the cellular level when combined. Therefore, the treatment with a composition comprising beta-sitosterol and resveratrol can provide inhibition of tumor cell growth and increased apoptosis. Furthermore, beta-sitosterol's potential stimulation the sphingomyelin cycle in prostate cancer cells by increased ROS activity may be mediated by resveratrol's antioxidant activity when the two are combined. In one embodiment, one or more additional antioxidant may be used to further reduce ROS activity.

In one embodiment, a subject may be treated with a composition that comprises one or more phytosterol and one or both of inositol hexaphosphate and an effective amount of one or more antioxidants that potentate 1,25-dihydroxy vitamin D ("D3"). In a further embodiment, the composition may comprise D3. As described herein, the sphingomyelin cycle is a pathway of signal transduction that plays a role in the control of cell growth, cell differentiation, and apoptosis. The sphingomyelin cycle may be stimulated when beta-sitosterol is incorporated into prostate cancer cells, which may lead to a balance between increased apoptosis and increased cancer cell growth to a point where the cancer may be stabilized at the level the balance is reached. This same activity may be used to explain the inhibition of tumor growth in mice and inhibition of the growth and metastasis of human breast cancer cells.

Both inositol hexaphosphate and D3 may be natural inducers of cell differentiation, and more specifically, inositol hexaphosphate may inhibit the in vitro growth of prostate cancer cells and induce differentiation in prostate cancer cells. Additionally, this same induction of cell differentiation may be desireable for normal prostate health and the combination of one or more phytosterol (in one embodiment a phytosterol composition comprising beta-sitosterol) and inositol hexaphosphate and D3 may be used for the prevention and treatment of benign prostatic hyperplasia.

As described herein, D3 may induce cell differentiation; however, the levels of D3 supplementation required for this to occur may produce hytercalcemia, which in some embodiments may limit therapeutic use. When one or more plant antioxidant is co-administered with D3, however, D3's ability to induce differentiation may be potentated. Therefore, in one embodiment, subjects may be treated with a composition that comprises effective amounts of antioxidants that potentates D3's ability to induce differentiation. In one embodiment, a subject may be treated with extracts from the following plants in an effective amount such that D3's ability to induce differentiation may be potentated: *Gynostemma pentaphyllum, Astragalus* root, *Rhodiola rosea, Ligustrum* fruit, *Polygonum cuspidatum, Punica granatum, punica granatum, Solanum lycopersicum, Rosmarinus officinalis* or various other organisms that comprise an antioxidant. Additionally, in a further embodiment a subject may be treated with one or more of the following compounds in an effective amount such that D3's ability to induce differentiation may be potentated, including, but not limited to: curcumin, or silibinin, lycopene, carnosic acid, various other antioxidants, and the like. In a still further embodiment, antioxidants or extracts from plants comprising antioxidants may be selected from a group that does not require a large volume of extract or antioxidant to produce potentation of D3. In a still further embodiment, one or more phytosterol along with antioxidants or extracts from plants comprising antioxidants may be selected to treat a subject for prostatitis and to promote prostate health by selecting one or more antioxidant or extract from a plant comprising an antioxidant, which synergistically produces anti-inflammatory properties. In one embodiment, synergistic anti-inflammatory antioxidants are selected from a the group of plant extracts and compounds, comprising, but not limited to *Gynostemma pentaphyllum, Astragalus* root, *Rhodiola rosea, Ligustrum* fruit, *Polygonum cuspidatum, Punica granatum, punica granatum, Solanum lycopersicum*, curcumin, silibinin, lycopene and the like.

(c) Antioxidants

Antioxidants are chemicals that reduce the rate of oxidation reactions, which are chemical reactions that involve the transfer of electrons from one substance to an oxidizing agent. Antioxidants may slow these reactions either by reacting with intermediates and halting the oxidation reaction directly, or by reacting with the oxidizing agent and preventing the oxidation reaction from occurring.

As described herein, beta-sitosterol may stimulate the sphingomyelin cycle in prostate cancer cells through increased reactive oxygen species ("ROS") activity, but this increase in ROS activity may be decreased by antioxidants. Therefore, in one embodiment, beta-sitosterol may be administered in a composition comprising complementary antioxidants to prevent an increase in ROS activity. In another embodiment, antioxidants or plant extracts comprising antioxidants may be selected to provide both a complement to beta-sitosterol and to specifically address cell membrane integrity, prostate health, hormone responsive tissue health, and general cellular health.

In a further embodiment, a subject may be treated with a composition comprising effective amounts of one or more phytosterol and extracts from the plant *Gynostemma pentaphyllum*. Extracts from the plant *Gynostemma pentaphyllum* may have antioxidant capacity by multiple antioxidant actions, may protect biomembranes from oxidative injury by reversing the decreased membrane fluidity, may decrease superoxidation anion and hydrogen peroxide content in neutrophils, and may inhibit peroxidation. Additionally, extracts from *Gynostemma pentaphyllum*, may induce apoptosis in hepatoma cells and colon cancer cells through a variety of pathways and may not produce toxicity in subjects, even at relatively high doses. In one embodiment, a subject may be treated with a composition comprising from about 3.41% to about 4.03% by weight of extract from *Gynostemma pentaphyllum*. In another embodiment a subject may be treated with a composition comprising from about 1.41% to about 6.03% by weight of extract from *Gynostemma pentaphyllum*.

In a still further embodiment, a subject may be treated with a composition comprising effective amounts of one or more phytosterol and extracts from the root of a plant of the genus *Astragalus*. Extracts from the root of a plant of the genus *Astragalus* may serve neuroprotective roles and direct antioxidant effects, stabilize cell membrane structures, and inhibit damage by glutamate. Pre-treatment of prostate cancer cells with extracts from the root of a plant of the genus *Astragalus* may increase the activities of antioxidant enzymes and may inhibit membrane lipid peroxidation. In one embodiment a subject may be treated with a composition comprising from about 2.56% to about 3.03% by weight of the extract from *Astragalus* root. In another embodiment a subject may be treated with a composition comprising from about 0.56% to about 5.03% by weight of the extract from *Astragalus* root. In a further embodiment, a subject may be treated with a composition comprising astragalosides, or an extract from a plant of the species *Radix Astragali*.

In a yet further embodiment, a subject may be treated with a composition comprising effective amounts of one or more phytosterol and salidroside. In another embodiment, salidroside may be from an extract of the plant *Rhodiola rosea*, or from a plant of the genus *Salix*. In one embodiment, a subject may be treated with a composition comprising effective amounts of one or more phytosterol, salidroside and extract from the root of a plant of the genus *Astragalus*. The combination of salidroside and extract from the root of a plant of the genus *Astragalus* may reduce lipid peroxidation and inhibit the accumulation of lactic acid in brain tissue and serum. In one embodiment, a subject may be treated with a composition comprising from about 1.70% to about 2.02% by weight of extract from *Rhodiola rosea*. In another embodiment a subject may be treated with a composition comprising from about 0.70% to about 4.02% by weight of extract from *Rhodiola rosea*.

In various embodiments, it may be desirable to treat a subject with a composition comprising salidroside, an extract of the plant *Rhodiola rosea*, an extract from a plant of the genus *Salix* because this may protect a cell (e.g. a cancer cell) against glutamate excitotoxic damage through suppressing the excessive entry of Ca2+ and the release of the calcium stores. This may help redress and maintain the calcium/magnesium balance and may apply to other cell types as well. This may be desirable because cancer appears to occur/metastasize when cells are rigid (e.g. excess structural cholesterol), Ca2+ levels are excessive, and there is insufficient Q10 available in the intracellular fluid, and possibly in the membrane itself.

In one embodiment, a subject may be treated with a composition comprising effective amounts of one or more extract from the following group: *Ligstrum* fruit, *Schisandra* fruit, *Punica granatum, Polygonum cuspidatum, Solanum lycopersicum, Elaeis*, and *Vitis*. Additionally, in another embodiment a subject may be treated with a composition comprising effective amounts of one or more compound from the following group: quersetin, lycopene, curcumin, silibinin, ellagic acid, and resveratrol.

In a still further embodiment a subject may be treated with a composition comprising effective amounts of quercetin and ellagic acid. This combination of compounds may synergistically induce apoptosis and transient cell cycle arrest in cancer cells. Additionally, in one embodiment, the composition may comprise an extract from *punica granatum*, which comprises about 70%, about 40% or about 10% by weight ellagic acid. In another embodiment the composition may comprise an extract from *punica granatum*, which comprises about 50% to about 90% by weight ellagic acid. In a further embodiment, ellagic acid can be obtained from strawberries, cranberries, walnuts, pecans, pomegranates, raspberries, or the like. In a still further embodiment the composition may further comprise resveratrol or an extract of the plant *Polygonum cuspidatum*, or an extract of the plant *polygonum cuspidatum* comprising about 15%, or about 2% by weight resveratrol. In yet another embodiment the composition may further comprise resveratrol or an extract of the plant *Polygonum cuspidatum*, or an extract of the plant *polygonum cuspidatum* comprises about 5% to about 25% by weight resveratrol.

In yet another embodiment, amounts of quercetin and ellagic acid in composition may be modeled after amounts of these compounds found in diets of subjects in areas of the world including, but not limited to the Mediterranean, China or Japan. Additionally, resveratrol may be added to such a composition in physiologically active levels, which may act synergistically as a chemopreventative agent, and to enhance the apoptotic activity of quercetin and ellagic acid.

In a yet another embodiment a subject may be treated with a composition comprising effective amounts of zinc and copper. Zinc and copper may promote proper expression of CuZn superoxide dismutase in a subject, which may protect healthy cells and suppress cancer growth. In one embodiment, the Zinc may be in the form of OptiZinc® manufactured by InterHealth Nutraceuticals a powdered 1:1 complex of zinc and methionine. In a further embodiment, trimethylglycince may be added in effective amounts, which may reduce or normalize homocystine levels, and thereby reduce or prevent cell injury from copper catalyzed hydrogen peroxide generation that may occur at elevated homocystine levels. Furthermore, in another embodiment, an effective amount of extract from *Astragalus* root may be added to the composition to inhibit oxidative stress induced by elevated levels of copper.

In another embodiment a subject may be treated with a composition comprising effective amounts of 3,3'-diindolylmethane or extract from *wasabia japonica*. This extract or compound may provide a sulforaphane analogue that activates the Nrf2-dependent detoxification pathway, which reduces general toxicity in the body and reduces the estrogen load by increasing the excretion of excess estrogens. Additionally, *wasabia japonica* may provide a chemoprotective effect.

from about 7.95% to about 7.06% by weight of 3,3'-diindolylmethane or from about 7.95% to about 7.06% by weight of extract from *wasabia japonica*. from about 9.95% to about 5.06% by weight of 3,3'-diindolylmethane or from about 9.95% to about 5.06% by weight of extract from *wasabia japonica*

In another embodiment, there may be one or more of the following proportions of compounds or extracts: from about 5.68% to about 5.05% by weight of quercetin; from about 1.70% to about 1.51% by weight of extract from *polygonum cuspidatum*; from about 7.95% to about 7.06% by weight of extract from *punica granatum*; from about 8.45% to about 8.57% by weight of inositol hexaphosphate; from about 3.41% to about 4.03% by weight of trimethylglycine; from about 0.57% to about 0.50% by weight of zinc; from about 0.06% to about 0.5% by weight of copper as gluconate; from about 2.56% to about 3.03% by weight of extract from *schisandra* fruit; from about 0.57% to about 0.50% by weight of lycopene; from about 2.13% to about 3.03% by weight of extract from *ligustrum* fruit; from about 7.95% to about 7.06% by weight of 3,3'-diindolylmethane or from about 7.95% to about 7.06% by weight of extract from *wasabia japonica*; from about 1.70% to about 1.51% by weight of one or more trocotrienol; from about 1.36% to about 1.61% by weight of one or more oligomeric proanthocyanidin; from about 5.68% to about 5.04% by weight of lecithin; from about 1.70% to about 2.02% by weight of extract from *rhodiola crenulata*. from about 40.88% to about 40.34% by weight of one or more species of phytosterol; from about 3.41% to about 4.03% by weight of extract from *gynostemma pentaphyllum*; from about 2.56% to about 3.03% by weight of extract from *astragalus* root; and from about 1.70% to about 1.51% by weight of extract from *polygonum cuspidatum*.

In yet another embodiment, there may be one or more of the following proportions of compounds or extracts: from about 7.68% to about 3.05% by weight of quercetin; from about 0.70% to about 3.51% by weight of extract from *polygonum cuspidatum*; from about 10.95% to about 4.06% by weight of extract from *punica granatum*; from about 6.45% to about 10.57% by weight of inositol hexaphosphate; from about 1.41% to about 6.03% by weight of trimethylglycine; from about 0.87% to about 0.20% by weight of zinc; from about 0.09% to about 0.2% by weight of copper as gluconate; from about 1.56% to about 4.03% by weight of extract from *schisandra* fruit; from about 0.87% to about 0.20% by weight of lycopene; from about 1.13% to about 4.03% by weight of extract from *ligustrum* fruit; from about 9.95% to about 5.06% by weight of 3,3'-diindolylmethane or from about 9.95% to about 5.06% by weight of extract from *wasabia japonica*; from about 2.70% to about 0.51% by weight of one or more trocotrienol; from about 0.36% to about 2.61% by weight of one or more oligomeric proanthocyanidin; from about 7.68% to about 3.04% by weight of lecithin; from about 0.70% to about 3.02% by weight of extract from *rhodiola crenulata*. from about 50.88% to about 30.34% by weight of one or more species of phytosterol; from about 2.41% to about 5.03% by weight of extract from *gynostemma pentaphyllum*; from about 1.56% to about 4.03% by weight of extract from *astragalus* root; and from about 2.70% to about 0.51% by weight of extract from *polygonum cuspidatum*.

(d) Methods of Administering to a Subject

In one embodiment, a combination of compounds and certain plants or herbs properly extracted and blended in appropriate proportions may used in treating cancer, prostate disorders, and promotion of cellular health, including but not limited to benign prostatic hyperplasia, prostatitis, prostate cancer, breast cancer, melanoma, glaucoma, and the like. Thus, various embodiments relate to methods for treating these diseases or disorders in a subject, comprising the step of administering an effective amount of a composition to said subject to treat or prevent a given disorder, wherein the composition comprises therapeutically effective amounts of compounds or extracts as described herein. In one embodiment, said composition may be administered orally. In another embodiment, an orally administered composition may be in the form of one or more capsules, one or more softgels, one or more tablets, or one or more pills.

The inventive methods use compositions which may be delivered to the patient by means of a pharmaceutically acceptable carrier. Such carriers are well known in the art and generally will be in either solid or liquid form. Solid form pharmaceutical preparations which may be prepared according to the present inventive subject matter include powders, tablets, dispersible granules, capsules, softgels and cachets. In general, solid form preparations may comprise from about 5% to about 90% by weight of the active agent; however, may comprise more or less in various embodiments.

A solid carrier may be one or more substance which may also act as a diluent, flavoring agent, solubilizer, lubricant, suspending agent, binder or tablet disintegrating agent; it may also be an encapsulating material. In powders, the carrier may be a finely divided solid which may be in admixture with the viscous active compound. In tablets, the active compound may be mixed with a carrier having the necessary binding properties in suitable proportions and compacted to the shape and size desired. Suitable solid carriers include magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term preparation may include the formulation of the active compound with encapsulating materials as a carrier which may provide a capsule or softgel in which the active component (with or without other carriers) may be surrounded by carrier, which is thus in association with it. Similarly, cachets are within the scope of various embodiments. Tablets, powders, cachets, softgels and capsules may be used as solid dosage forms suitable for oral administration. If desired for reasons of convenience or patient acceptance, pharmaceutical tablets prepared according to various embodiments may be provided in chewable form, using techniques well known in the art.

In some embodiments, suitable carriers may be solid form preparations which are intended to be converted, shortly before use, to liquid form preparations for either oral or parenteral administration. Such liquid forms include solutions, suspensions, and emulsions. These particular solid form preparations may be provided in unit dose form and as such may be used to provide a single liquid dosage unit. Alternately, sufficient solid may be provided so that after conversion to liquid form, multiple individual liquid doses may be obtained by measuring predetermined volumes of the liquid form preparation as with a syringe, teaspoon, or other volumetric container. When multiple liquid doses are so prepared, it may be desireable to maintain the unused portion of said liquid doses at low temperature (i.e., under refrigeration) in order to retard possible decomposition. The solid form preparations intended to be converted to liquid form may contain, in addition to the active material, flavorants, colorants, stabilizers, buffers, artificial and natural sweeteners, dispersants, thickeners, solubilizing agents, and the like. The liquid utilized for preparing useful liquid form preparations may be water, isotonic water, ethanol, glycerine, propylene glycol, and the like as well as mixtures thereof. The liquid utilized may be chosen with regard to the route of administration. For example, liquid preparations containing large amounts of ethanol may not be suitable for parenteral use.

The pharmaceutical preparation may also be in a unit dosage form. In such form, the preparation may be subdivided into unit doses containing appropriate quantities of the active component. The unit dosage form may be a packaged preparation, the package containing discrete quantities of preparation, for example, packeted tablets, softgels, capsules, and powders in vials or ampoules. The unit dosage form may also be a capsule, softgel, cachet, or tablet itself, or the like, or it may be the appropriate number of any of these in packaged form.

In various embodiments, a pharmaceutical preparation may be provided in one or more capsule, softgel, cachet, tablet, or the like. Although a given dosing regimen may be provided in a consistent dose formulation, in some embodiments, the amount of various compounds of a given preparation may be changed or be absent in different doses, capsules, or the like. For example, a preparation may include compounds A, B, X and Y, and a patient may be treated with two capsules every two hours wherein a first capsule comprises compounds A and B and a second capsule comprises compounds X and Y. Alternatively, a patient may be treated with one capsule every hour, wherein a capsule comprising A and B is provided every other hour and a capsule comprising X and Y is provided otherwise.

Accordingly, it should be clear to one of ordinary skill in the art that compositions and methods according to various embodiments described herein need not always be administered in the same dosage, or in a single capsule, or the like, to be within the scope and spirit of the embodiments disclosed herein. Therefore, the terms composition, therapeutic composition, pharmaceutical composition, and the like should be construed to include the average dose over a period of, or a dose provided in one or more discrete capsule, softgel, cachet, or tablet, or the like.

The pharmaceutical preparations of various embodiments may include one or more preservatives well known in the art, such as benzoic acid, sorbic acid, methylparaben, propylparaben, ethylenediaminetetraacetic acid (EDTA), and the like. Preservatives are generally present in amounts up to about 1% and preferably from about 0.05% to about 0.5% by weight of the pharmaceutical composition; however, preservatives may be present in various other amounts in other embodiments.

Useful buffers for purposes of the inventive subject matter include citric acid-sodium citrate, phosphoric acid-sodium phosphate, and acetic acid-sodium acetate in amounts up to about 1% and preferably from about 0.05 to about 0.5% by weight of the pharmaceutical composition. Useful suspending agents or thickeners include cellulosics like methylcellulose, carageenans like alginic acid and its derivatives, xanthan gums, gelatin, acacia, and microcrystalline cellulose in amounts up to about 20% and preferably from about 1% to about 15% by weight of the pharmaceutical composition, and the like.

Sweeteners which may be employed include those sweeteners, both natural and artificial, that are well known in the art. Sweetening agents such as monosaccharides, disaccharides and polysaccharides such as xylose, ribose, glucose, mannose, galactose, fructose, dextrose, sucrose, maltose, partially hydrolyzed starch or corn syrup solids and sugar alcohols such as sorbitol, xylitol, mannitol, and the like. Such mixtures thereof, in one embodiment, may be utilized in amounts from about 10% to about 60% or from about 20% to about 50% by weight of the pharmaceutical composition. Water soluble artificial sweeteners such as saccharin and saccharin salts such as sodium or calcium, cyclamate salts, acesulfame-K, aspartame and the like and mixtures thereof may be utilized, for example, in amounts from about 0.001% to about 5% by weight of the composition.

Flavorants which may be employed in various embodiments, which includes both natural and artificial flavors, and mints such as peppermint, menthol, vanilla, artificial vanilla, chocolate, artificial chocolate, cinnamon, various fruit flavors, both individually and mixed, in amounts from about 0.5% to about 5% by weight of the pharmaceutical composition.

Colorants useful in various embodiments includes pigments which may be incorporated in amounts of up to about 6% by weight of the composition. For example, titanium dioxide, may be incorporated in amounts up to about 1%. Also, the colorants may include other dyes suitable for food, drug and cosmetic applications, known as F.D.&C. dyes and the like. In one embodiment, such dyes may be present in amounts up to about 0.25% or from about 0.05% to about 0.2% by weight of the pharmaceutical composition. A full recitation of all F.D.&C. and D.&C. dyes and their corresponding chemical structures may be found in the Kirk-Othmer Encyclopedia of Chemical Technology, in Volume 5, at pages 857 884, which text is accordingly incorporated herein by reference. Useful solubilizers include alcohol, propylene glycol, polyethylene glycol and the like and may be used to solubilize the flavors. Solubilizing agents may be present in amounts up to about 10% in one embodiment.

Lubricating agents which may be used when desired in the instant compositions include silicone oils or fluids such as substituted and unsubstituted polysiloxanes, e.g., dimethyl polysiloxane, also known as dimethicone. Other well known lubricating agents may be employed.

In some embodiments, it is desireable for compositions to not display significant adverse interactions with other synthetic or naturally occurring substances. Thus, a compound or composition as described herein may be administered in combination with other compounds and compositions useful for treating cancer, prostate disorders, and promotion of cellular health, including but not limited to benign prostatic hyperplasia, prostatitis, prostate cancer, breast cancer, melanoma, and glaucoma. Some embodiments use compositions which may be administered in combination with other compositions, other antineoplastic substances, and the like.

The optimal pharmaceutical formulations may be determined by one skilled in the art depending upon considerations such as the route of administration and desired dosage. See, for example, "Remington's Pharmaceutical Sciences", 18th ed. (1990, Mack Publishing Co., Easton, Pa. 18042), pp. 1435 1712, which is hereby incorporated by reference in its entirety. Such formulations may influence the physical state, stability, rate of in vivo release, and rate of in vivo clearance of the present therapeutic agents of the inventive subject matter.

Additionally, a specific dose level for a particular patient may depend upon a variety of factors, including the activity of the specific compound employed; the age, body weight, general health, sex and diet of the patient; the time of administration; the rate of excretion; drug combination; the severity of the particular disorder being treated; and the form of administration. One of ordinary skill in the art would appreciate the variability of such factors and would be able to establish specific dose levels using no more than routine experimentation.

TABLE 1 depicts an exemplary composition that may be used to treat human male subjects for diseases or disorders, including but not limited to, prostate cancer, prostatitis, benign prostatic hyperplasia, or other cancer. Additionally, this composition may be used to treat a subject for diseases or disorders, including but not limited to various types of cancer or to treat a subject to promote cellular health. In one embodiment, this exemplary composition may be used to treat human female subjects.

TABLE 2 depicts an exemplary composition that may be used to treat female human subject for diseases including breast cancer or various other types cancer and to promote cellular health. Additionally, this composition may be used to promote cellular health in a subject. In one embodiment, this exemplary composition may be used to treat human male subjects. As depicted in TABLE 1 and 2, effective ranges of compounds or extracts displayed with a slash ("/") represent amounts in milligrams of concentrated herb or plant and equivalent amount in raw powdered herb or plant in milligram on the left and right of the slash respectively.

EXAMPLES

The following examples are included to demonstrate preferred embodiments. It should be appreciated by those of skill in the art that the techniques disclosed in the examples which follow represent techniques discovered to function well, and thus may be considered to constitute preferred modes for its practice. Those skilled in the art, however, should in light of the disclosure, appreciate that many changes can be made in the specific embodiments which are disclosed and still obtain a like or similar result without departing from the spirit and scope of the embodiments.

In the following non-limiting examples, a composition (hereinafter "PMC Formula") was used comprising: 15 mg extract from *Gynostemma pentaphyllum;* 11.25 mg extract from the root of *Astragalus;* 9.62 mg extract from the fruit of *Ligustrum;* 25 mg extract from the fruit of *Schisandra;* 7.5 mg of extract from *Rhodiola crenulata;* 35 mg of extract from *Punica granatum* comprising about 70% by weight ellagic acid; 7.5 mg of extract from *Polygonum cuspidatum* comprising about 15% by weight resveratrol, 25 mg quesrcitin; about 180 mg of phytosterol complex comprising at least 50% by weigh beta-sitosterol and further comprising beta-sitostanol; 37.19 mg inositol hexaphosphate; 15 mg trimethylglycine; 6 mg OPC grape seed extract; 2.5 mg lycopene extract comprising about 15% by weigh lycopene; 2.5 mg 1-OptiZinc® powder manufactured by InterHealth Nutraceuticals a powdered 1:1 complex of zinc and methionine: 0.25 mg copper as gluconate; and 25 mg lecithin powder.

Example 1

Treatment for Benign Prostatic Hyperplasia

One thousand (1000) human subjects who had each been diagnosed with benign prostatic hyperplasia were treated with the PMC Formula for a period of at least three months. Subjects were treated exclusively with eight doses of the PMC Formula orally per day, spread out over the day. Within three months almost all patients exhibited an amount of variable positive results.

Example 2

Treatment for Low Grade Prostate Cancer

Three hundred (300) human subjects who had each been diagnosed with low-grade prostate cancer were treated exclusively with the PMC Formula for a period of at least three months. Subjects were treated with ten (10) doses of the PMC Formula orally per day, spread out over the day. Within three months, 95% of subjects exhibited either stabilization or regression of their low-grade prostate cancer. The only noted side effect in some patients was transient nausea.

Example 3

Treatment for Prostatitis

Five (5) human subjects who had each been diagnosed with prostatitis were treated exclusively with the PMC Formula for a period of at least three months. Subjects were treated with twelve (12) doses of the PMC Formula orally per day, spread out over the day. Within three months, 80% of subjects exhibited reduced prostatitis. The only noted side effect in some patients was transient nausea.

Example 4

Treatment for High Grade Prostate Cancer

Ninety (90) human subjects who had each been diagnosed with high-grade prostate cancer were treated with the PMC Formula for a period of at least three months. Subjects were treated with fourteen (14) doses of the PMC Formula orally per day, spread out over the day. Within three months, 85% of subjects exhibited either stabilization or regression of their high-grade prostate cancer. The only noted side effect in some patients was transient nausea.

FIG. 1 depicts an image of the prostate of an exemplary subject before treatment with the PMC Formula. The subject was diagnosed with high-grade prostate cancer, which is depicted in FIG. 1. At this time, the subject was found to have significantly elevated levels of prostate-specific antigen (PSA) of 33 ng/ml, and a Gleason score of 7.

Figure 2:
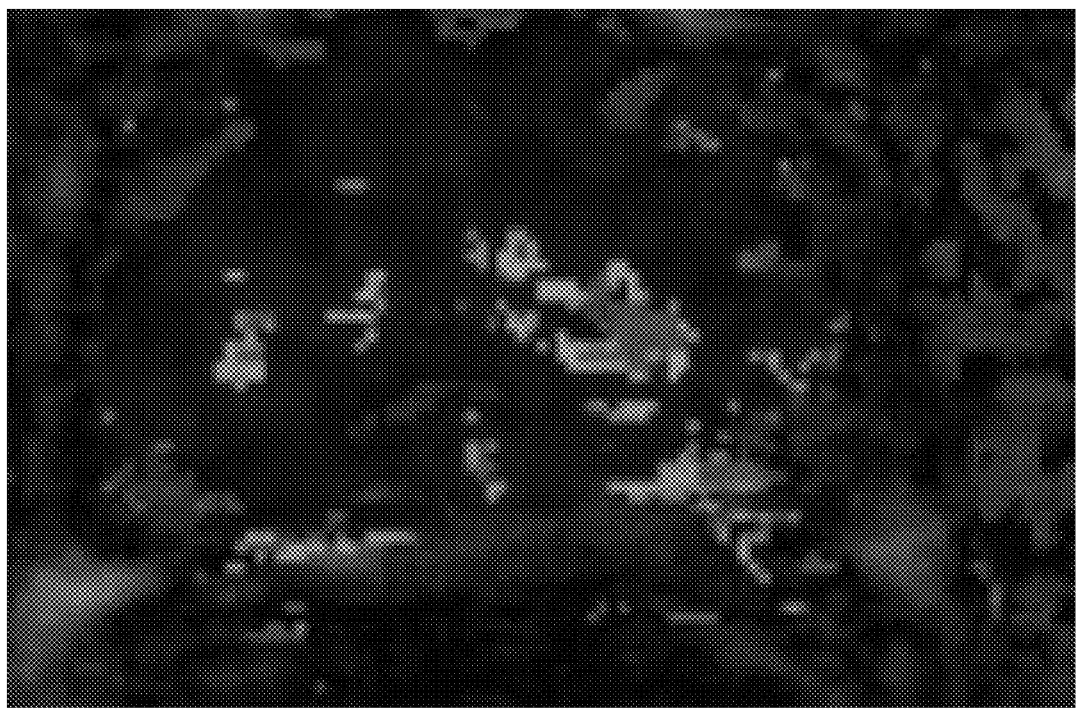
FIG. 2 depicts an image of the prostate of the exemplary subject in FIG. 1 after treatment with a therapeutic composition, in accordance with an embodiment.

FIG. 2 depicts an image of the prostate of the same subject as depicted in FIG. 1 which was taken approximately three months after the image in FIG. 1 was taken and after treatment with the PMC Formula. As shown in FIG. 2, the subject exhibited a significant regression of the prostate cancer and reduced tumor vascularity, which are surrogate endpoints for prostate cancer survival. Additionally, the subject was found to have greatly reduced (PSA) levels of 6 ng/ml, which is only slightly elevated compared to normal levels of PSA.

Example 5

Treatment for Breast Cancer

Figure 3:
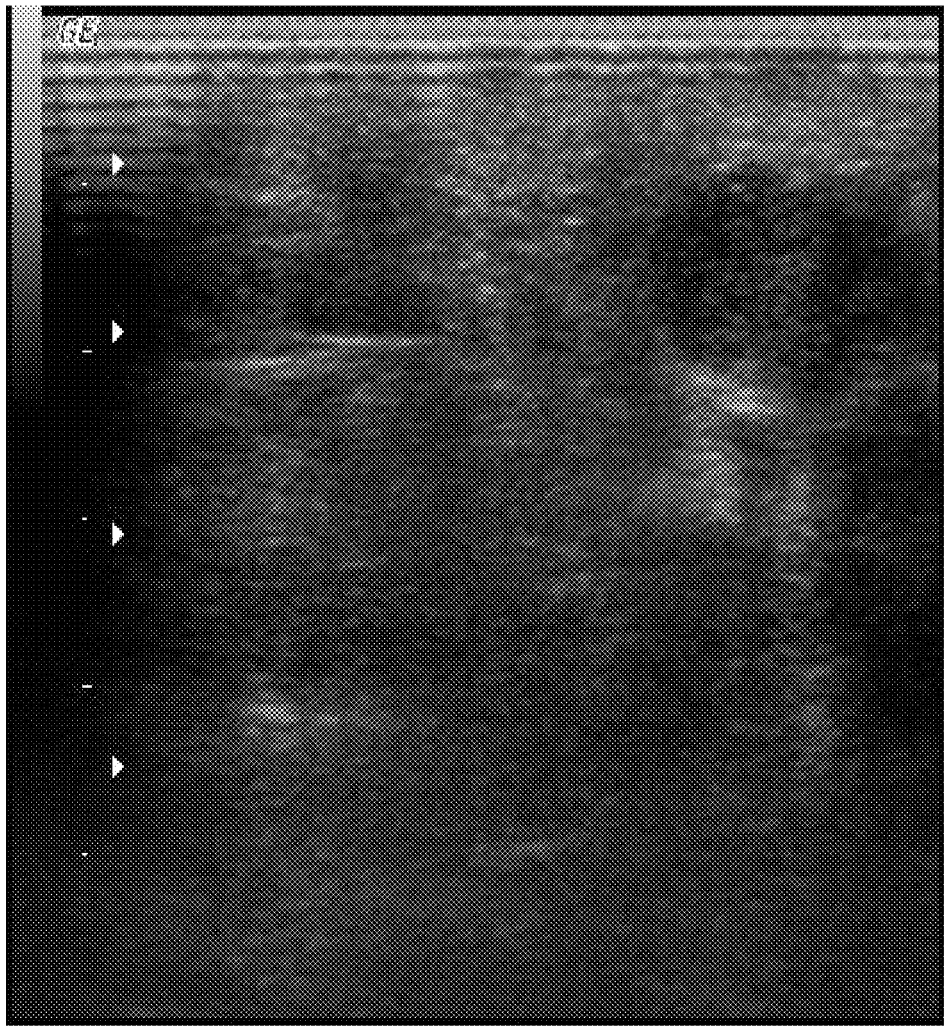
FIG. 3 depicts an image of a breast tumor of a subject before treatment with a therapeutic composition in accordance with an embodiment.
Figure 4:
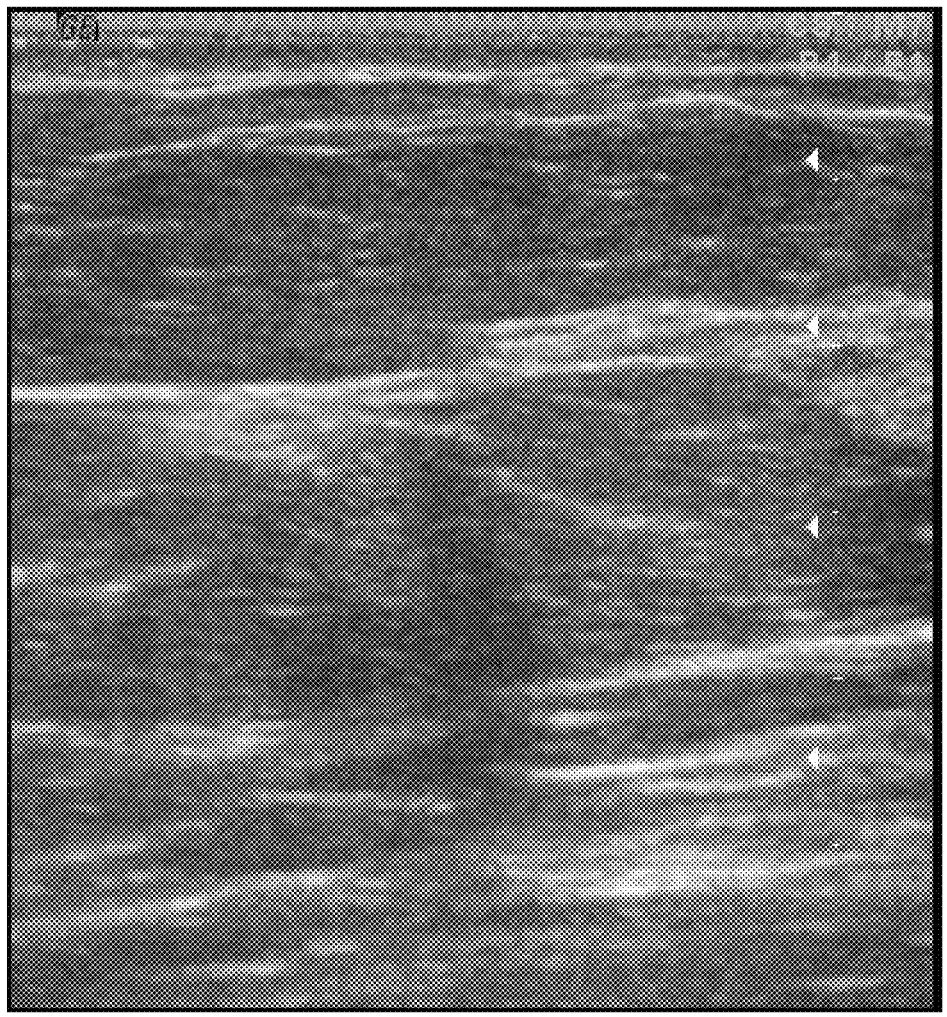
FIG. 4 depicts an image of the same breast of the same subject depicted in FIG. 3 after treatment with a therapeutic composition in accordance with an embodiment.

One female human subject who had been diagnosed with breast cancer was treated exclusively with the PMC Formula for a period of six months. The subject was given ten (10) doses of the PMC Formula orally per day, spread out over the day. The subject exhibited stabilization of her breast cancer within 3 months and continued stabilization of her breast cancer for an additional 6 months. FIG. 3 depicts an image of breast cancer of the subject before treatment with the PMC Formula, and FIG. 4 depicts and image of the same breast of the same subject after treatment with the PMC Formula.

Example 6

Treatment for Melanoma

One human subject who had been diagnosed with melanoma was treated exclusively with the PMC Formula for a period of three months. The subject was given fourteen (14) doses of the PMC Formula orally per day, spread out over the day. The subject exhibited stabilization of the melanoma over a period of three months.

Example 7

Treatment for Glaucoma

One human subject who had been diagnosed with glaucoma was treated exclusively treated with the PMC Formula for a period of three months. The subject was given ten (10) doses of the PMC Formula orally per day, spread out over the day. The subject exhibited stabilization of glaucoma within 3 months.

While preferred and alternate embodiments of the invention have been illustrated and described, as noted above, many changes may be made without departing from the spirit and scope of the invention. Accordingly, the scope of the invention is not limited by the disclosure of these preferred and alternate embodiments. Instead, the invention should be determined by reference to the claims that follow.

Example 8

Treatment for Diabetes

Two human subjects who had been diagnosed with diabetes were added exclusively eight (8) doses PMC Formula orally per day, spread out over the day. Both subjects noted almost immediate reduction of their required insulin dosage by approximately 50%.

Example 8

Treatment of Prostate Cancer

Figure 5:
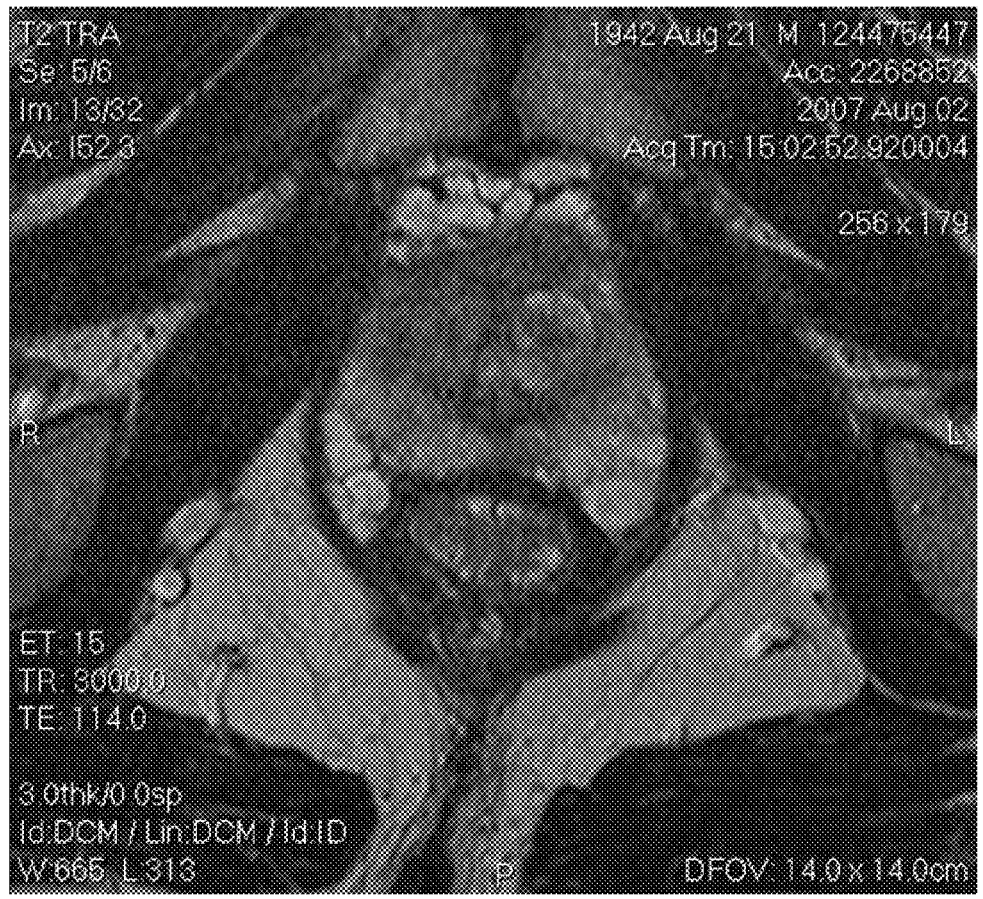
FIG. 5 depicts a pre-treatment MRI of a first subject, in accordance with an embodiment.
Figure 6:
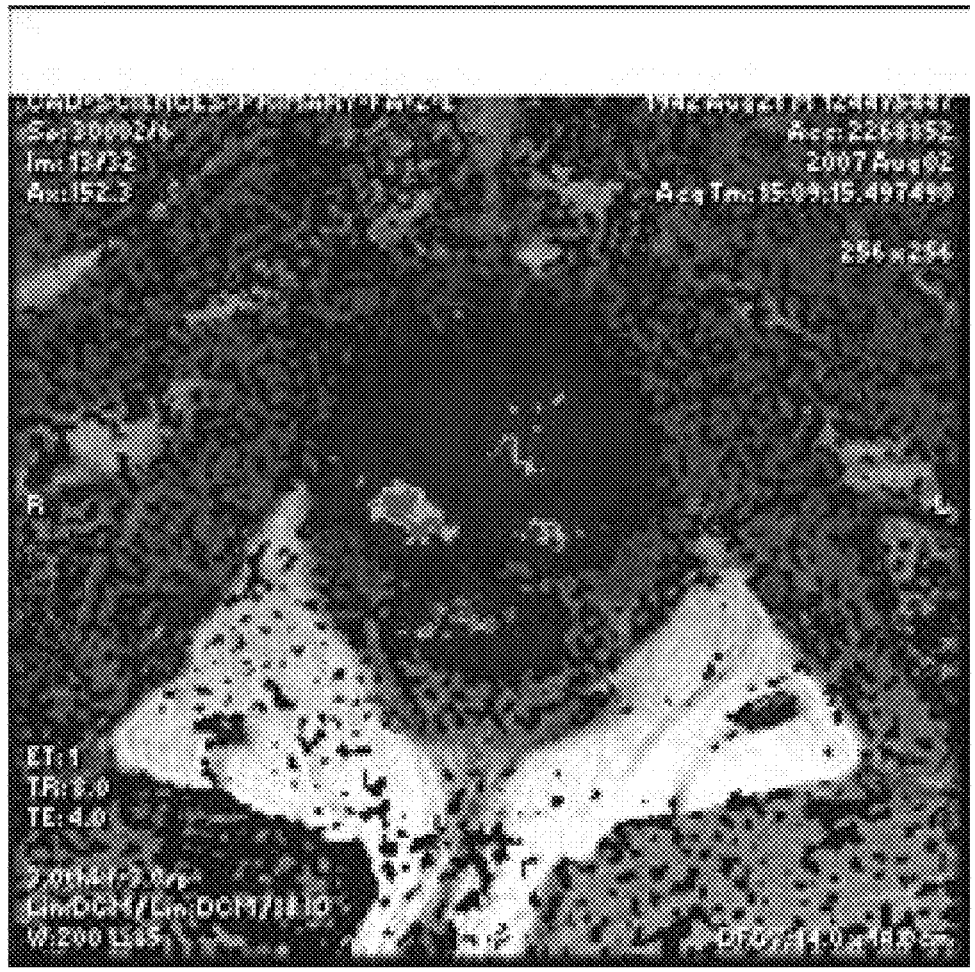
FIG. 6 depicts a pre-treatment color MRI of the first subject, in accordance with an embodiment.
Figure 7:
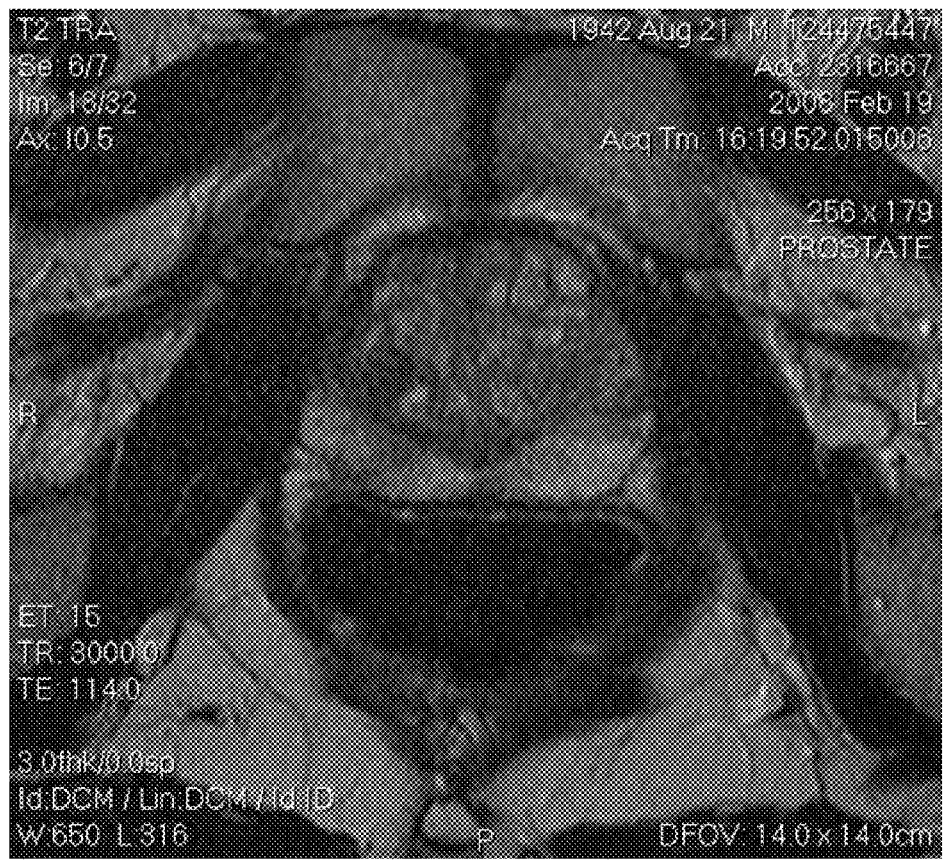
FIG. 7 depicts a post-treatment MRI of the first subject, in accordance with an embodiment.
Figure 8:
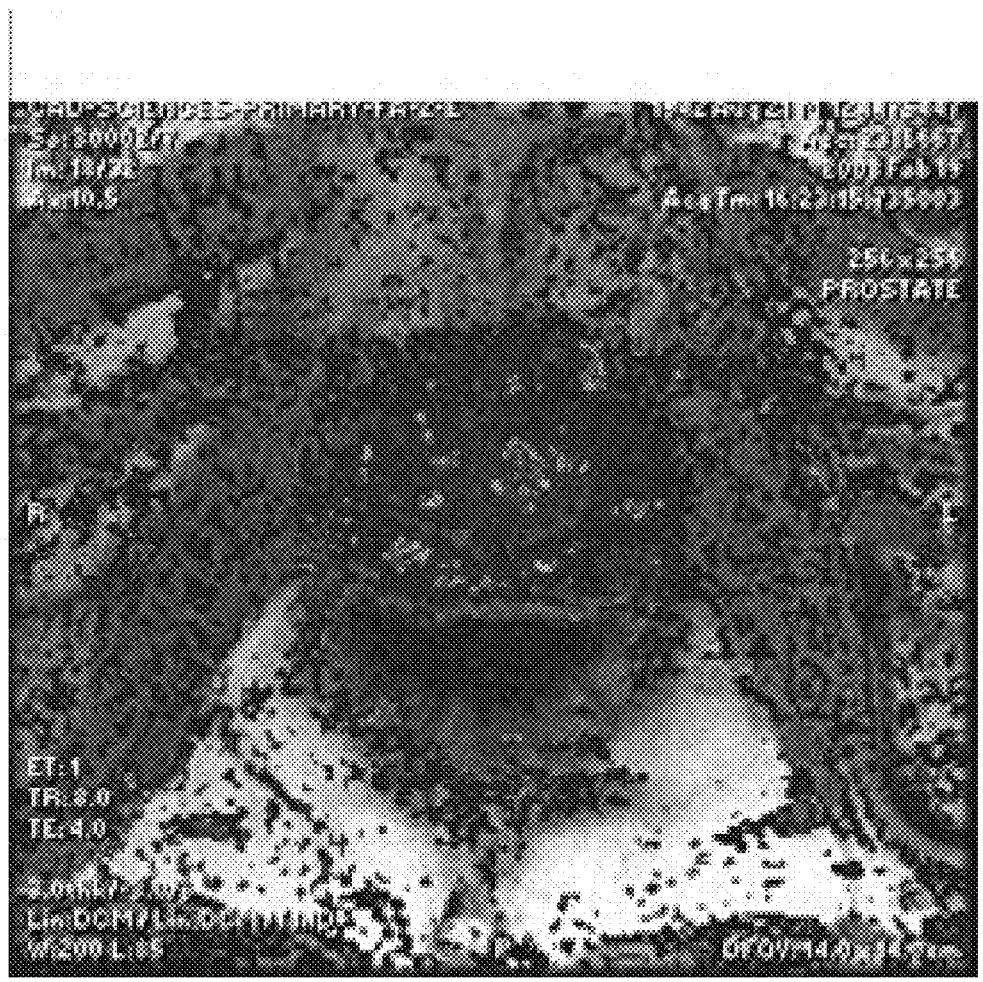
FIG. 8 depicts a post-treatment color MRI of the first subject, in accordance with an embodiment.

A 60 year-old subject who had been diagnosed with high-grade prostate cancer with a Gleason score of 8 was treated exclusively with the PMC Formula for a period of 4 months. Subject was treated with fourteen (14) doses of the PMC Formula orally per day, spread out over the day. FIG. 5 depicts a pre-treatment MRI; FIG. 6 depicts a pre-treatment color MRI; FIG. 7 depicts a post-treatment MRI; FIG. 8 depicts a post-treatment color MRI. Color contrast MRI changes specify from 65% to 96% (NY Acad Medicine 2008). Subject showed 90% improvement. The only noted side effect was transient nausea.

Example 9

Treatment of Prostate Cancer

Figure 9:
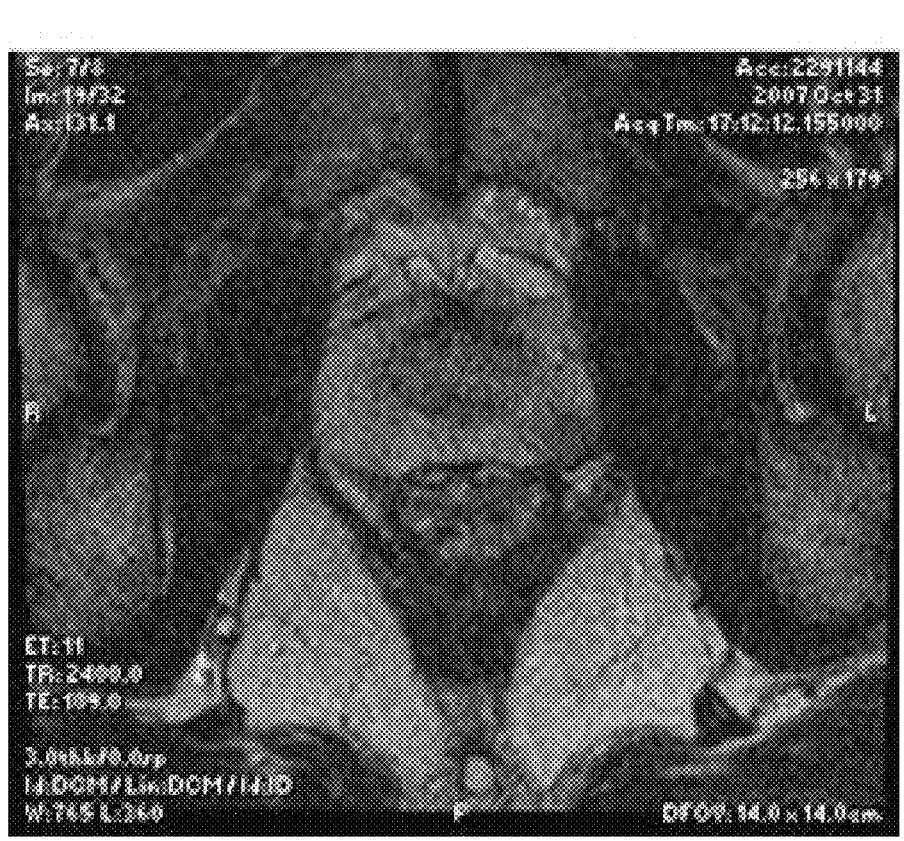
FIG. 9 depicts a pre-treatment MRI of a second subject, in accordance with an embodiment.
Figure 10:
FIG. 10 depicts a pre-treatment color MRI of the second subject, in accordance with an embodiment.
Figure 11:
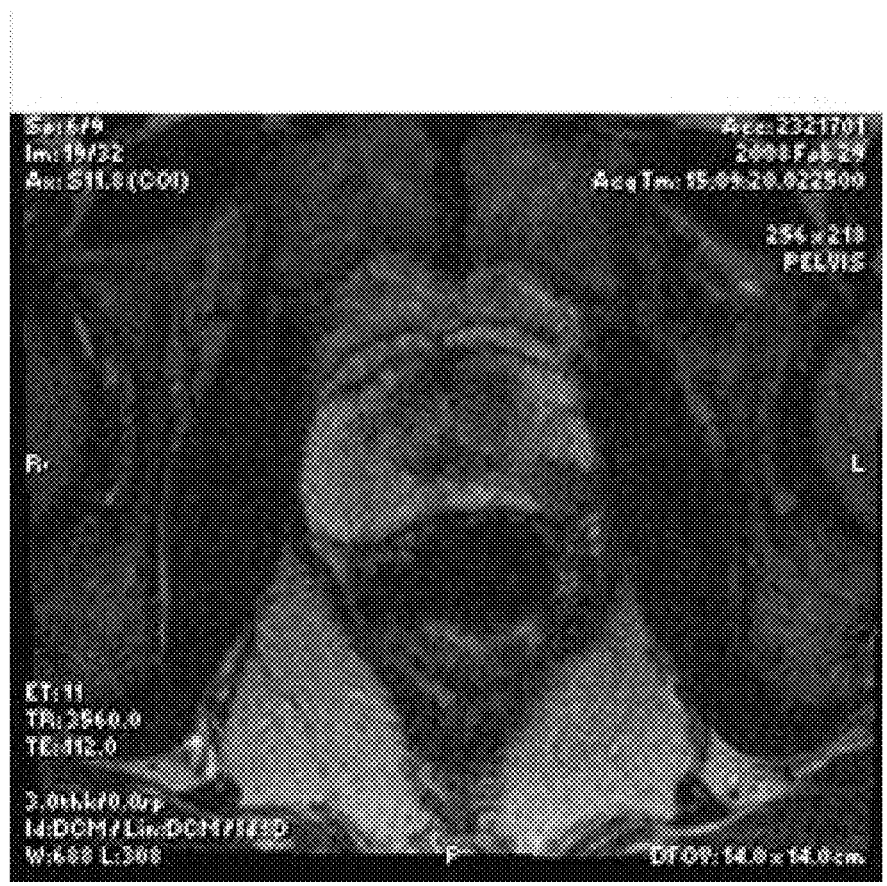
FIG. 11 depicts a post-treatment MRI of the second subject, in accordance with an embodiment.
Figure 12:
FIG. 12 depicts a post-treatment color MRI of the second subject, in accordance with an embodiment.

A 70 year-old subject who had been diagnosed with high-grade prostate cancer with a Gleason score of 9 was treated exclusively with the PMC Formula for a period of 4 months. Subject was treated with fourteen (14) doses of the PMC Formula orally per day, spread out over the day. FIG. 9 depicts a pre-treatment MRI; FIG. 10 depicts a pre-treatment color MRI; FIG. 11 depicts a post-treatment MRI; FIG. 12 depicts a post-treatment color MRI. Color contrast MRI changes specify from 65% to 96% (NY Acad Medicine 2008). Subject showed 20% improvement. The only noted side effect was transient nausea.

Example 10

Treatment of Prostate Cancer

Figure 13:
FIG. 13 depicts a pre-treatment MRI of a third subject, in accordance with an embodiment.
Figure 14:
FIG. 14 depicts a pre-treatment color MRI of the third subject, in accordance with an embodiment.
Figure 15:
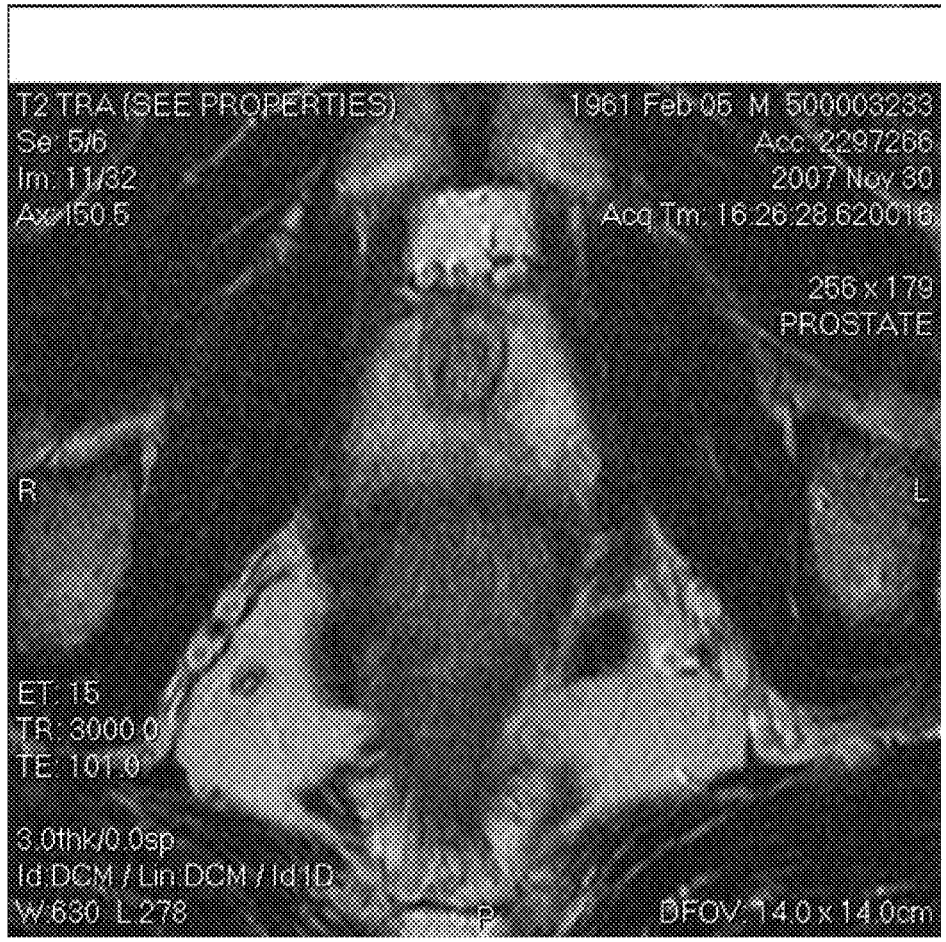
FIG. 15 depicts a post-treatment MRI of the third subject, in accordance with an embodiment.
Figure 16:
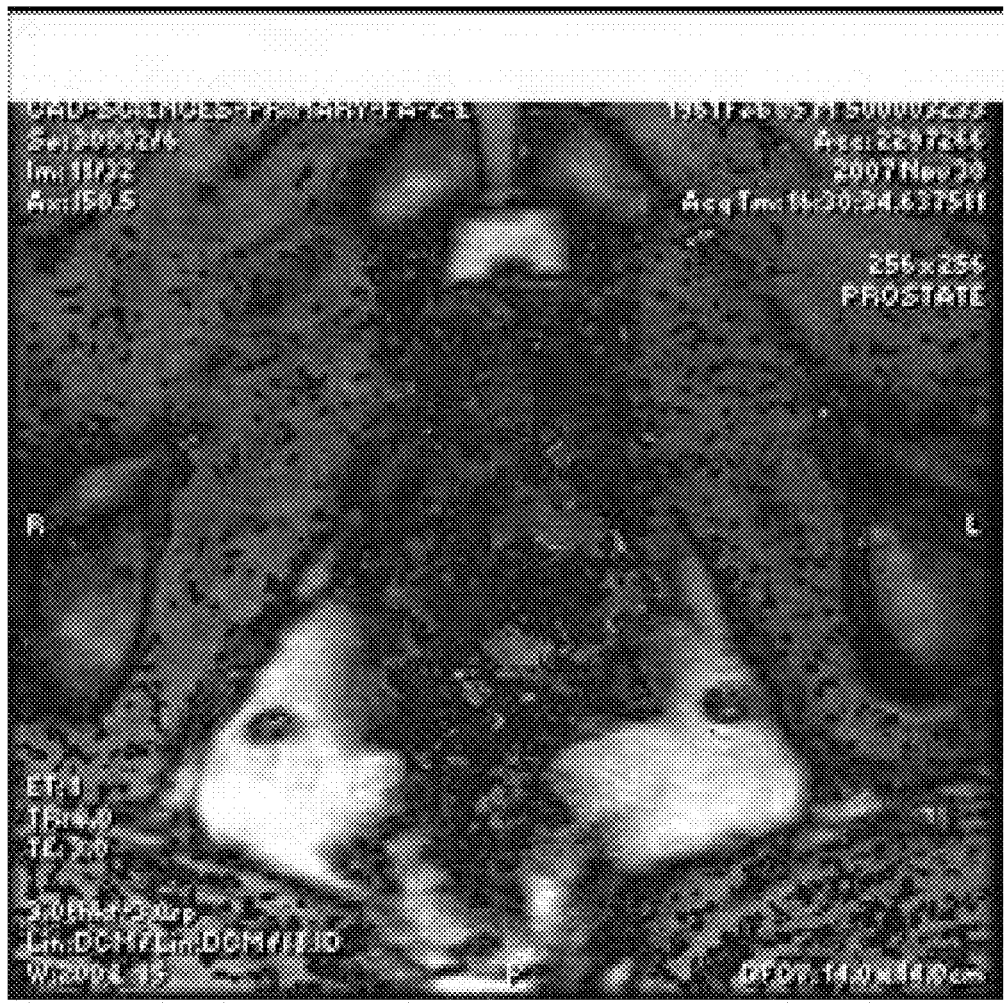
FIG. 16 depicts a post-treatment color MRI of the third subject, in accordance with an embodiment.

A 75 year-old subject who had been diagnosed with intermediate-grade prostate cancer with a Gleason score of 7 was treated exclusively with the PMC Formula for a period of 9 months. Subject was treated with fourteen (14) doses of the PMC Formula orally per day, spread out over the day. FIG. 13 depicts a pre-treatment MRI; FIG. 14 depicts a pre-treatment color MRI; FIG. 15 depicts a post-treatment MRI; FIG. 16 depicts a post-treatment color MRI. Color contrast MRI changes specify from 65% to 96% (NY Acad Medicine 2008). Subject showed 80% improvement. The only noted side effect was transient nausea.

Example 11

Treatment of Prostate Cancer

Figure 17:
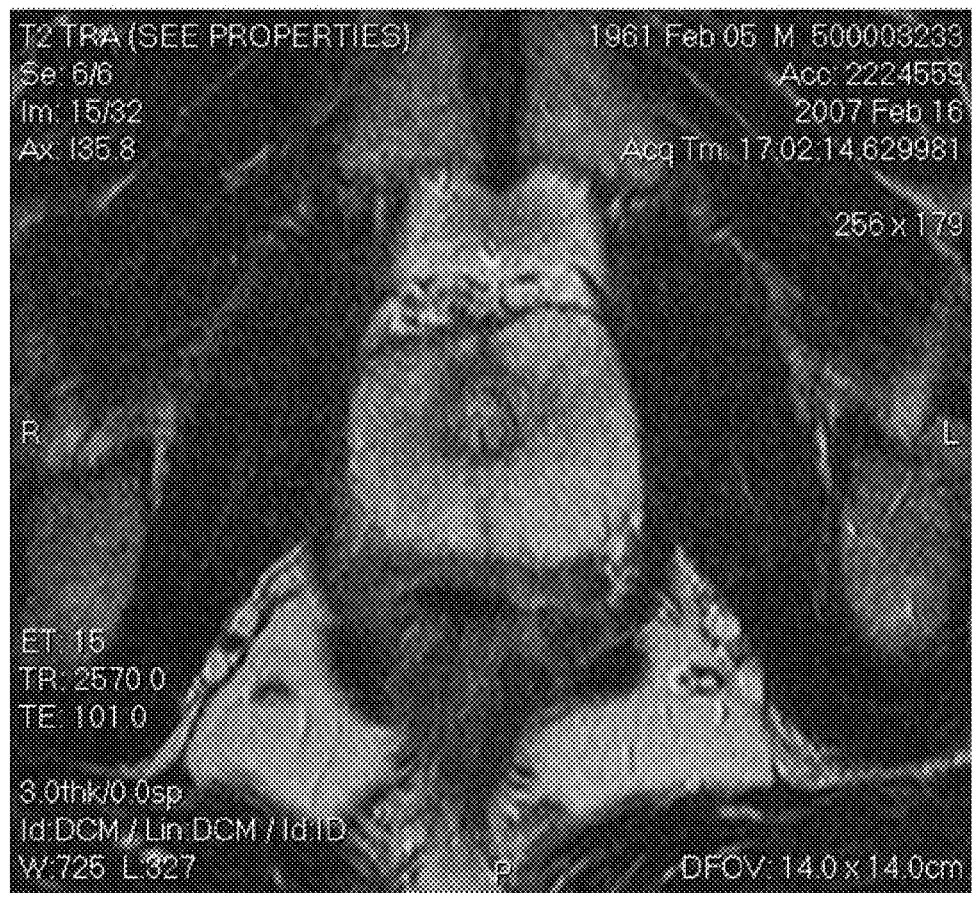
FIG. 17 depicts a pre-treatment MRI of a fourth subject, in accordance with an embodiment.
Figure 18:
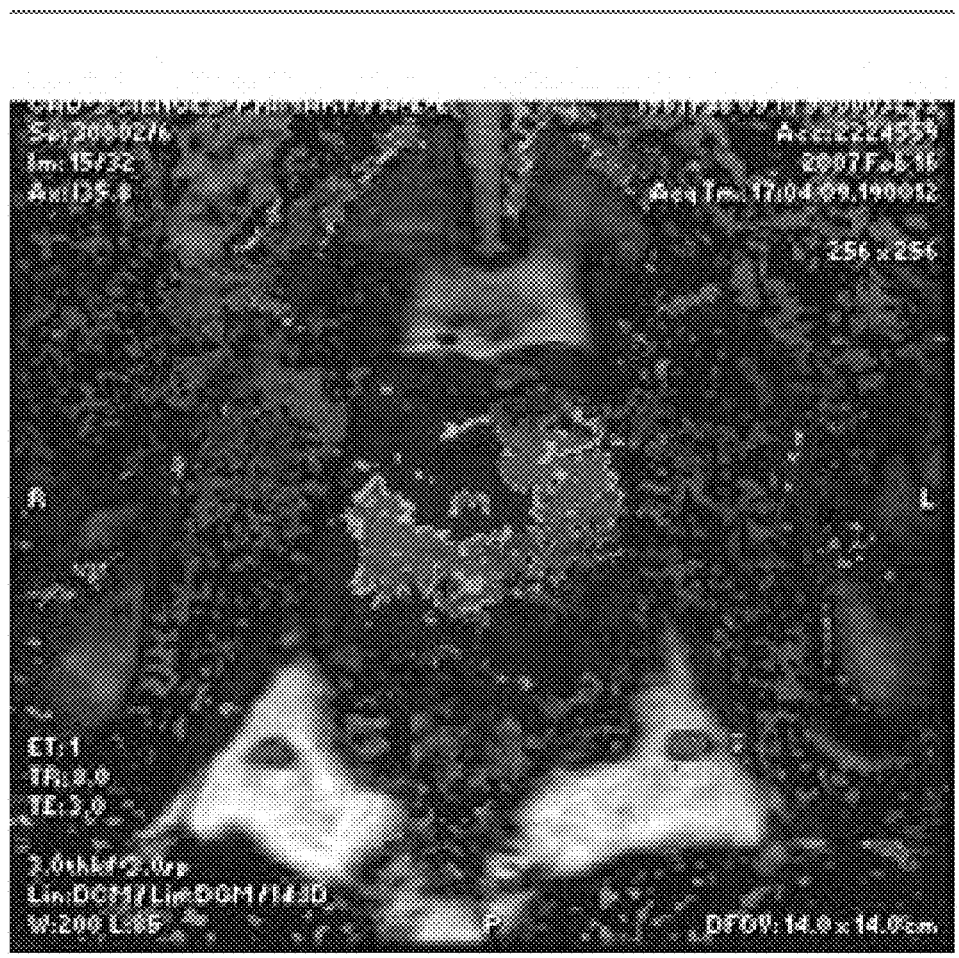
FIG. 18 depicts a pre-treatment color MRI of the fourth subject, in accordance with an embodiment.
Figure 19:
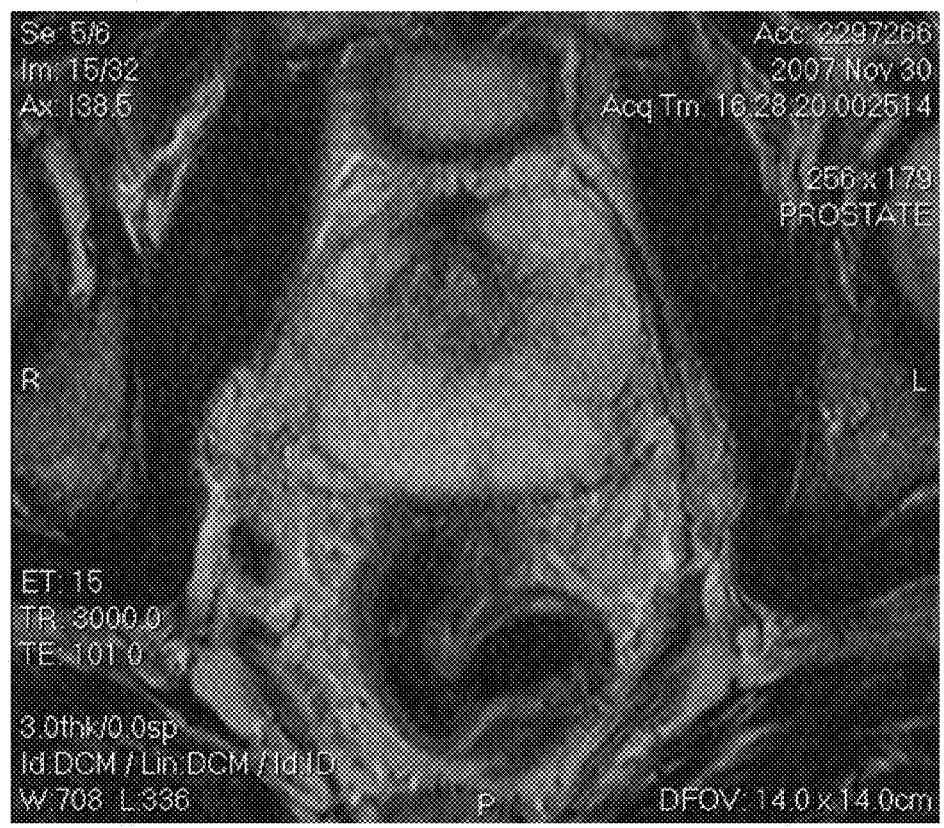
FIG. 19 depicts a post-treatment MRI of the fourth subject, in accordance with an embodiment.
Figure 20:
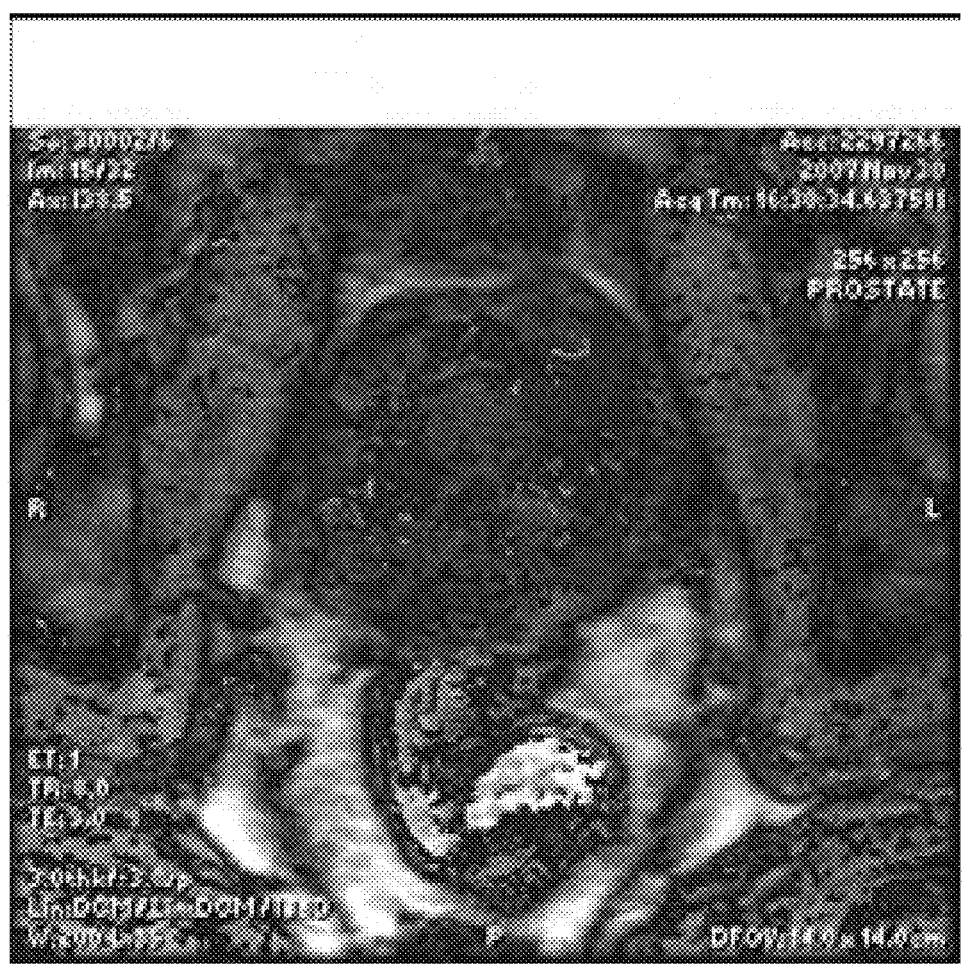
FIG. 20 depicts a post-treatment color MRI of the fourth subject, in accordance with an embodiment.

A 65 year-old subject who had been diagnosed with intermediate-grade prostate cancer with a Gleason score of 6 was treated exclusively with the PMC Formula for a period of 9 months. Subject was treated with fourteen (14) doses of the PMC Formula orally per day, spread out over the day. FIG. 17 depicts a pre-treatment MRI; FIG. 18 depicts a pre-treatment color MRI; FIG. 19 depicts a post-treatment MRI; FIG. 20 depicts a post-treatment color MRI. Color contrast MRI changes specify from 65% to 96% (NY Acad Medicine 2008). Subject showed 90% improvement. The only noted side effect was transient nausea.

Example 12

Treatment of Prostate Cancer

Figure 21:
FIG. 21 depicts a pre-treatment MRI of a fifth subject, in accordance with an embodiment.
Figure 22:
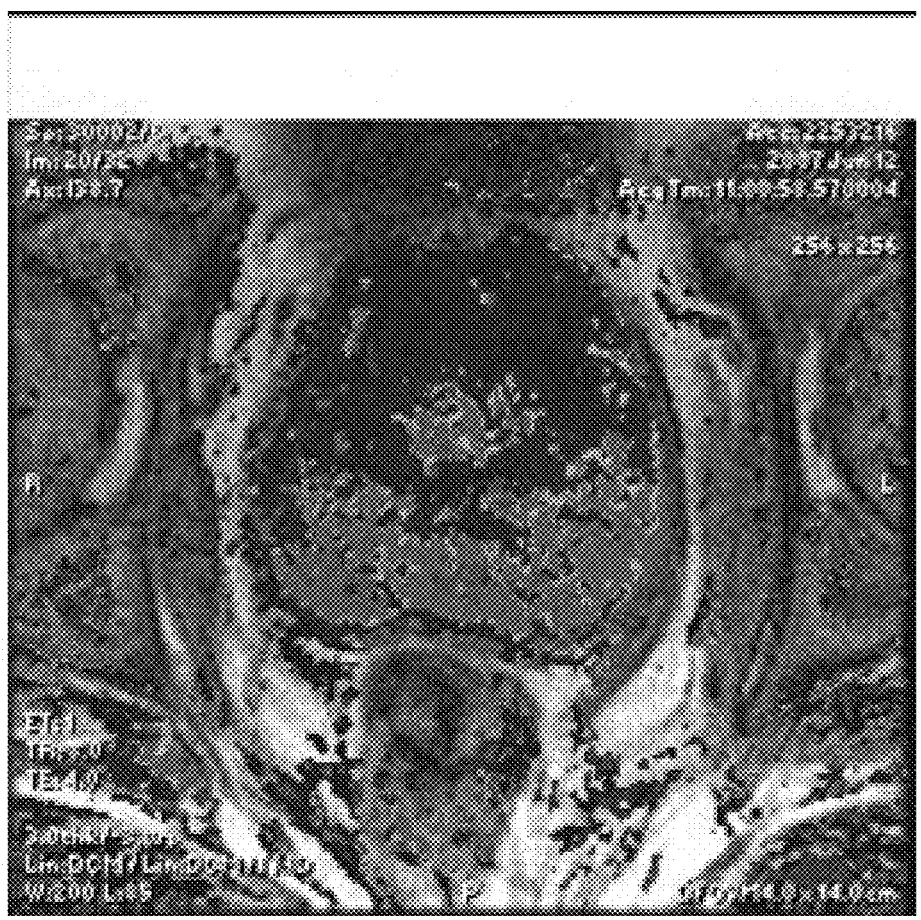
FIG. 22 depicts a pre-treatment color MRI of the fifth subject, in accordance with an embodiment.
Figure 23:
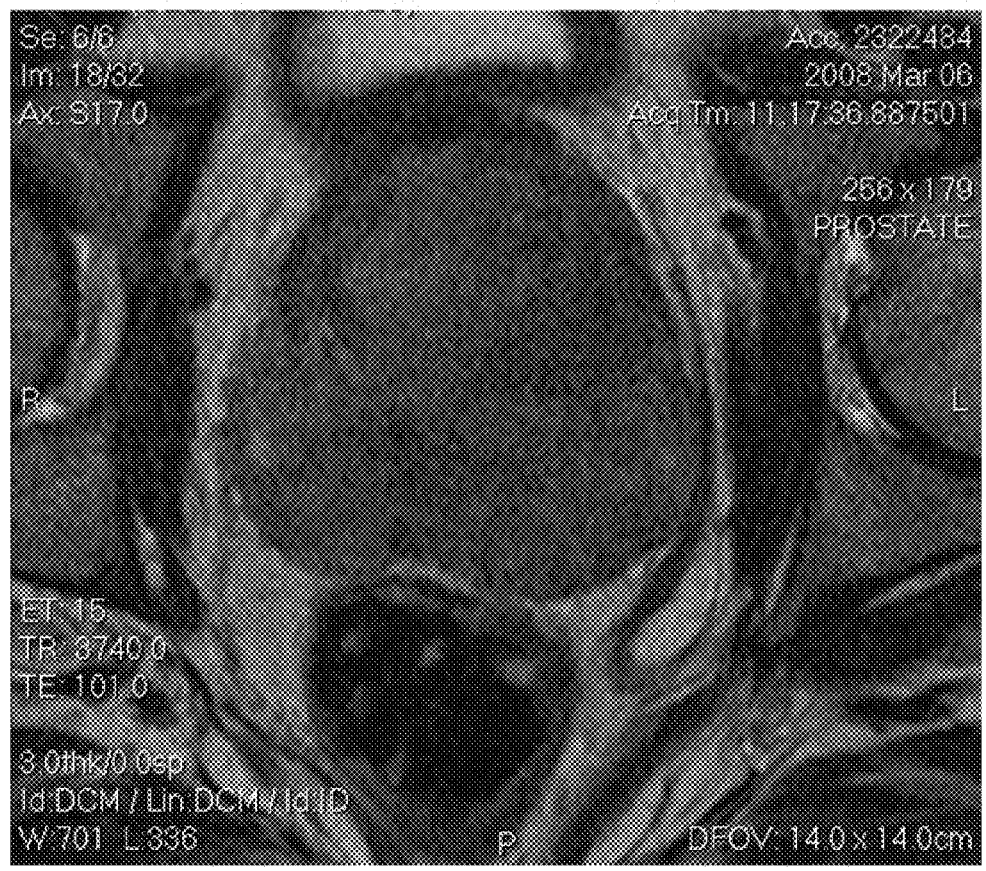
FIG. 23 depicts a post-treatment MRI of the fifth subject, in accordance with an embodiment.
Figure 24:
FIG. 24 depicts a post-treatment color MRI of the fifth subject, in accordance with an embodiment.

A 55 year-old subject who had been diagnosed with intermediate-grade prostate cancer with a Gleason score of 7 was treated exclusively with the PMC Formula for a period of 9 months. Subject was treated with fourteen (14) doses of the PMC Formula orally per day, spread out over the day. FIG. 21 depicts a pre-treatment MRI; FIG. 22 depicts a pre-treatment color MRI; FIG. 23 depicts a post-treatment MRI; FIG. 24 depicts a post-treatment color MRI. Color contrast MRI changes specify from 65% to 96% (NY Acad Medicine 2008). Subject showed 70% improvement. The only noted side effect was transient nausea.

Although specific embodiments have been illustrated and described herein, it will be appreciated by those of ordinary skill in the art and others, that a wide variety of alternate and/or equivalent implementations may be substituted for the specific embodiment shown in the described without departing from the scope of the embodiments described herein. This application is intended to cover any adaptations or variations of the embodiment discussed herein. While various embodiments have been illustrated and described, as noted above, many changes may be made without departing from the spirit and scope of the embodiments described herein.

The invention claimed is:

1. A pharmaceutical composition consisting essentially of:
   15 mg extract of *Gynostemma pentaphyllum*;
   11.25 mg extract of the root of *Astragalus*;
   9.62 mg extract of the fruit of *Ligustrum*;
   25 mg extract of the fruit of *Schisandra*;
   7.5 mg of extract of *Rhodiola crenulata*;
   35 mg of extract of *Punica granatum* comprising about 70% by weight ellagic acid;
   7.5 mg of extract of *Polygonum cuspidatum* comprising about 15% by weight resveratrol;
   25 mg quercetin;
   about 180 mg of phytosterol complex comprising at least 50% by weight beta-sitosterol and further comprising beta-sitostanol;
   37.19 mg inositol hexaphosphate;
   15 mg trimethylglycine;
   6 mg oligomeric proanthocyanidin grape seed extract;
   2.5 mg *Solanum lycopersicum* extract comprising about 15% lycopene;
   2.5 mg powdered 1:1 complex of zinc and methionine;
   0.25 mg copper as gluconate; and
   25 mg lecithin powder.

* * * * *